US008623396B2

(12) United States Patent
Gray et al.

(10) Patent No.: US 8,623,396 B2
(45) Date of Patent: Jan. 7, 2014

(54) COMPOSITIONS AND METHODS FOR DELIVERING CLONIDINE AND BUPIVACAINE TO A TARGET TISSUE SITE

(75) Inventors: Jonathan K. Gray, Collierville, TN (US); Jeffrey C. Marx, Germantown, TN (US); William F. McKay, Memphis, TN (US); Josee Roy, Memphis, TN (US); Danielle L. Clay, Collierville, TN (US); Jared T. Wilsey, Memphis, TN (US); John Myers Zanella, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 26 days.

(21) Appl. No.: 13/310,240

(22) Filed: Dec. 2, 2011

(65) Prior Publication Data
US 2012/0142649 A1 Jun. 7, 2012

Related U.S. Application Data

(60) Provisional application No. 61/419,510, filed on Dec. 3, 2010.

(51) Int. Cl.
A61F 2/00 (2006.01)
A61K 9/00 (2006.01)

(52) U.S. Cl.
CPC .................................. A61K 9/0024 (2013.01)
USPC ....................................................... 424/424

(58) Field of Classification Search
None
See application file for complete search history.

(56) References Cited

U.S. PATENT DOCUMENTS

| | | |
|---|---|---|
| 4,624,255 A | 11/1986 | Schenck et al. |
| 4,742,054 A | 5/1988 | Naftchi |
| 4,863,457 A | 9/1989 | Lee |
| 5,522,844 A | 6/1996 | Johnson |
| 5,626,838 A | 5/1997 | Cavanaugh, Jr. |
| 5,759,583 A | 6/1998 | Iwamoto et al. |
| 5,868,789 A | 2/1999 | Huebner |
| 5,942,241 A | 8/1999 | Chasin et al. |
| 5,980,927 A | 11/1999 | Nelson et al. |
| 6,069,129 A | 5/2000 | Sandberg et al. |
| 6,179,862 B1 | 1/2001 | Sawhney |
| 6,248,345 B1 | 6/2001 | Goldenheim et al. |
| 6,287,588 B1 | 9/2001 | Shih et al. |
| 6,326,020 B1 | 12/2001 | Kohane et al. |
| 6,331,311 B1 | 12/2001 | Brodbeck et al. |
| 6,428,804 B1 | 8/2002 | Suzuki et al. |
| 6,451,335 B1 | 9/2002 | Goldenheim et al. |
| 6,461,631 B1 | 10/2002 | Dunn et al. |
| 6,524,607 B1 | 2/2003 | Goldenheim et al. |
| 6,534,081 B2 | 3/2003 | Goldenheim et al. |
| 6,589,549 B2 | 7/2003 | Shih et al. |
| 6,630,155 B1 | 10/2003 | Chandrashekar et al. |
| 6,632,457 B1 | 10/2003 | Sawhney |
| 6,699,908 B2 | 3/2004 | Sackler et al. |
| 6,723,741 B2 | 4/2004 | Jeon et al. |
| 6,756,058 B2 | 6/2004 | Brubaker et al. |
| 6,773,714 B2 | 8/2004 | Dunn et al. |
| 6,921,541 B2 | 7/2005 | Chasin et al. |
| 6,974,462 B2 | 12/2005 | Sater |
| 7,144,412 B2 | 12/2006 | Wolf et al. |
| 7,166,570 B2 | 1/2007 | Hunter et al. |
| 7,220,281 B2 | 5/2007 | Lambrecht et al. |
| 7,229,441 B2 | 6/2007 | Trieu et al. |
| 7,235,043 B2 | 6/2007 | Gellman et al. |
| 7,287,983 B2 | 10/2007 | Ilan |
| 7,318,840 B2 | 1/2008 | McKay |
| 7,329,259 B2 | 2/2008 | Cragg |
| 7,361,168 B2 | 4/2008 | Makower et al. |
| 7,367,978 B2 | 5/2008 | Drewry et al. |
| 2001/0037104 A1 | 11/2001 | Zhang et al. |
| 2002/0009454 A1 | 1/2002 | Boone et al. |
| 2002/0090398 A1 | 7/2002 | Dunn et al. |
| 2003/0144570 A1 | 7/2003 | Hunter et al. |
| 2003/0185873 A1 | 10/2003 | Chasin et al. |
| 2003/0204191 A1 | 10/2003 | Sater et al. |
| 2003/0224033 A1 | 12/2003 | Li et al. |
| 2004/0072799 A1 | 4/2004 | Li et al. |
| 2004/0082540 A1 | 4/2004 | Hermida Ochoa |
| 2004/0109893 A1 | 6/2004 | Chen et al. |

(Continued)

FOREIGN PATENT DOCUMENTS

| | | |
|---|---|---|
| WO | 03005961 A2 | 1/2003 |
| WO | 2005034998 A2 | 4/2005 |

OTHER PUBLICATIONS

Atrigel, Drug Delivery Platform, QLT USA, Inc., Revised Jul. 2006, 2 pages.
Elizabeth A. Moberg-Wolff, MD, Spasticity, Updated Dec. 21, 2007, pp. 1-15.
Daniel P. Moore, Helping your patients with spasticity reach maximal function, vol. 104, No. 2, Aug. 1998, www.postgradmed.com/issue/1998/08_98/moore.thm., pp. 1-9.

(Continued)

Primary Examiner — Bethany Barham
(74) Attorney, Agent, or Firm — Sorell Lenna & Schmidt LLP

(57) ABSTRACT

Effective treatments of pain for extended periods of time are provided. Through the administration of an effective amount of immediate release bupivacaine or lidocaine and a sustained release clonidine at or near a target site, one can relieve pain caused by diverse sources, including but not limited to spinal disc herniation (i.e. sciatica), spondilothesis, stenosis, discogenic back pain and joint pain. When appropriate formulations are provided within biodegradable polymers, this relief can be continued for at least three days. In some embodiments, the relief can be for at least twenty-five days, at least fifty days, at least one hundred days, at least one hundred and thirty-five days or at least one hundred and eighty days or longer.

20 Claims, 4 Drawing Sheets

(56) References Cited

U.S. PATENT DOCUMENTS

| | | |
|---|---|---|
| 2004/0214793 A1 | 10/2004 | Hermida Ochoa |
| 2005/0079202 A1 | 4/2005 | Chen et al. |
| 2005/0142163 A1 | 6/2005 | Hunter et al. |
| 2005/0175709 A1 | 8/2005 | Baty, III et al. |
| 2005/0177135 A1 | 8/2005 | Hildebrand et al. |
| 2005/0186261 A1 | 8/2005 | Avelar et al. |
| 2005/0197293 A1 | 9/2005 | Mellis et al. |
| 2006/0074422 A1 | 4/2006 | Story et al. |
| 2006/0106361 A1 | 5/2006 | Muni et al. |
| 2006/0148903 A1 | 7/2006 | Burch et al. |
| 2006/0183786 A1 | 8/2006 | Wang |
| 2006/0189944 A1 | 8/2006 | Campbell et al. |
| 2006/0228391 A1 | 10/2006 | Seyedin et al. |
| 2007/0156180 A1 | 7/2007 | Jaax et al. |
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2007/0248639 A1 | 10/2007 | Demopulos et al. |
| 2007/0253994 A1 | 11/2007 | Hildebrand |
| 2008/0021074 A1 | 1/2008 | Cartt |
| 2008/0091207 A1 | 4/2008 | Truckai et al. |
| 2009/0202436 A1* | 8/2009 | Hobot et al. ............... 424/1.65 |
| 2009/0246123 A1 | 10/2009 | Zanella et al. |
| 2009/0263319 A1 | 10/2009 | Wohabrebbi et al. |
| 2009/0263321 A1 | 10/2009 | Mcdonald et al. |
| 2009/0263443 A1 | 10/2009 | King |
| 2009/0264491 A1 | 10/2009 | Mckay et al. |
| 2010/0015049 A1 | 1/2010 | Wohabrebbi |
| 2010/0160375 A1* | 6/2010 | King ............................ 514/315 |

OTHER PUBLICATIONS

International Search Report and Written Opinion for PCT/US2011/063159, the counterpart application mailed on Jul. 9, 2012.

* cited by examiner

COMPOSITIONS AND METHODS FOR DELIVERING CLONIDINE AND BUPIVACAINE TO A TARGET TISSUE SITE

This application claims the benefit of the filing date of U.S. Provisional Patent Application Ser. No. 61/419,510, filed on Dec. 3, 2010. This entire disclosure is hereby incorporated by reference into the present disclosure.

BACKGROUND

Pain is typically experienced when the free nerve endings of pain receptors are subject to mechanical, thermal, chemical or other noxious stimuli. These pain receptors can transmit signals along afferent neurons to the central nervous system and then to the brain. When a person feels pain, any one or more of a number of problems can be associated with this sensation, including but not limited to reduced function, reduced mobility, complication of sleep patterns, and decreased quality of life.

One known type of pain is radicular pain, which refers to pain that radiates along the dermatome of a nerve. This pain may be due to inflammation or other irritation of the nerve root at its connection to the spinal column. A common form of radiculitis is sciatica, or radicular pain that radiates along the sciatic nerve from the lower spine to the lower back, gluteal muscles, back of the upper thigh, calf, and foot as often secondary to nerve root irritation from a spinal disc herniation or from bone spurs or ostophytes in the lumbar region of the spine.

The causes of pain include but are not limited to inflammation, injury, disease, muscle stress, the onset of a neuropathic event or syndrome, and damage that can result from surgery or an adverse physical, chemical or thermal event or from infection by a biologic agent. When a tissue is damaged, a host of endogenous pain inducing substances, for example, bradykinin and histamine can be released from the injured tissue. The pain inducing substances can bind to receptors on the sensory nerve terminals and thereby initiate afferent pain signals. After activation of the primary sensory afferent neurons, the projection neurons may be activated. These neurons carry the signal via the spinothalamic tract to higher parts of the central nervous system.

One known class of pharmaceuticals to treat pain is opioids. This class of compounds is well-recognized as being among the most effective type of drugs for controlling pain, such as post-operative pain. Unfortunately, because opioids are administered systemically, the associated side effects raise significant concerns, including disabling the patient, depressing the respiratory system, constipation, and psychoactive effects such as sedation and euphoria, thereby instituting a hurdle to recovery and regained mobility. Consequently, physicians typically limit the administration of opioids to within the first twenty-four hours post-surgery. Thus, it would be preferable to use non-narcotic drugs that deliver direct, localized pain control at a surgical site.

One pharmaceutical that is known to the medical profession is clonidine, which is widely recognized as an antihypertensive agent that acts as an agonist on the alpha-2-adrenergic receptor and as a neural receptor agonist. In general, clonidine, also referred to as 2,6-dichloro-N-2-imidazolidinyldenebenzenamine ($C_9H_9Cl_2N_3$) may be represented by the following chemical structure:

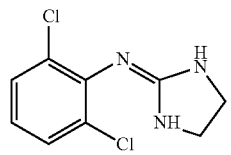 [SMILES: Clc1cccc(Cl)c1N=C1NCCN1]

Another pharmaceutical that is known to the medical profession is bupivacaine, which is widely recognized as a local anesthetic for infiltration, nerve block, epidural and intrathecal administration. In general, bupivacaine, also referred to as 1-butyl-N-(2,6-dimethylphenyl) piperidine-2-carboxamide ($C_{18}H_{28}N_2O$) may be represented by the following structure:

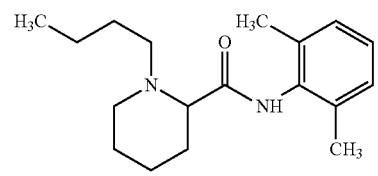 [SMILES: CCCCN1CCCCC1C(=O)Nc1c(C)cccc1C]

Another pharmaceutical that is known to the medical profession is lidocaine, which is widely recognized local anesthetic. Lidocaine is also a class Ib antiarrhythmic agent, blocking the sodium channel of the cardiac action potential, which reduces the slope of phase 0 of depolarization with little effect on the PR interval, QRS complex or QT interval.

There have been numerous proposals for which active ingredients are most effective for treating pain, including radicular pain. Because different active ingredients, and different vehicles for administering them have different benefits and risks, there is a need to develop better compositions and methods for administering active ingredients in different vehicles to treat pain at the same target site.

SUMMARY

Compositions and methods are provided comprising administering a drug depot having an immediate release region to provide a bolus dose of bupivacaine and/or lidocaine and a sustained release region to provide sustained release of the clonidine over an extended period of time. In some embodiments, separate depots are administered, where one set of depots allows for immediate release of bupivacaine and/or lidocaine and a second set of depots allows for sustained release of clonidine. In some embodiments, a sustained release drug depot comprising clonidine is administered to a target tissue site, before, during or with an immediate release bupivacaine and/or lidocaine formulations to treat pain at a target tissue site. In some embodiments, the immediate release formulation can be in solution form.

The compositions and methods provided may, for example, be used to treat pain due to a spinal disc herniation (i.e., sciatica), spondilothesis, stenosis, osteoarthritis, carpal/tarsal tunnel syndrome, tendonitis, temporomandibular joint disorder (TMJ), discogenic back pain, joint pain or inflammation.

In some embodiments, by combining the drug depot with a one-time bupivacaine and/or lidocaine injection, a patient can obtain the acute benefits of a bupivacaine and/or lidocaine injection while receiving more sustained analgesia from the clonidine depot and avoid the tissue-damaging effects of multiple clonidine injections.

In one embodiment, there is an implantable drug depot useful for reducing, preventing or treating pain in a patient in need of such treatment, the implantable drug depot comprising 0.1 wt % to about 30 wt % clonidine, 15 wt % to about 60 wt % bupivacaine or 0.1 wt % to about 30 wt % or 15 wt % to about 30 wt % lidocaine and a biodegradable polymer, the depot being implantable at a site beneath the skin to reduce, prevent or treat pain, wherein the drug depot comprises (i) at least one region capable of releasing a therapeutically effective bolus dose of the bupivacaine or lidocaine at a site beneath the skin; and (ii) at least one sustained release region capable of releasing a therapeutically effective amount of the clonidine over a period of at least three days.

In another embodiment, there is an implantable drug depot useful for reducing or treating pain in a patient in need of such treatment, the implantable drug depot comprising clonidine, bupivacaine or lidocaine and a biodegradable polymer in amorphous, crystalline or semicrystalline form; wherein the crystalline form may include polymorphs, solvates or hydrates.

In another embodiment, there is a kit comprising a plurality of implantable drug depots useful for reducing, preventing or treating pain in a patient in need of such treatment, the kit comprising a first set of the plurality of drug depots comprising a biodegradable polymer capable of releasing a therapeutically effective bolus dose of bupivacaine or lidocaine at a site beneath the skin and a second set of the plurality of drug depots comprising a second biodegradable polymer capable of providing sustained release of a therapeutically effective amount of the clonidine over a period of at least three days.

In another embodiment, the kit comprises an immediate release component that is a solution. In some embodiments, the immediate and sustained release formulations are packaged together or separately. In some embodiments, the immediate and sustained release formulations are found in separate kits that include instructions on how to use the combined treatment.

In yet another embodiment, there is a method for treating a mammal suffering from pain, the method comprising administering a therapeutically effective amount of an injectable bupivacaine or lidocaine and an implantable device comprising clonidine in an amount from about 0.1 wt. % to about 30 wt. % of the implantable device, and at least one biodegradable polymer, wherein the implantable device is capable of releasing clonidine over a period of at least three days.

The drug depot may: (i) consist of only the clonidine, bupivacaine, and/or lidocaine (or one or more of its pharmaceutically acceptable salts) and the biodegradable polymer(s); or (ii) consist essentially of the clonidine, bupivacaine, and/or lidocaine (and/or one or more of its pharmaceutically acceptable salts) and the biodegradable polymer(s); or (iii) comprise the clonidine, bupivacaine, and/or lidocaine (and/or one or more of its pharmaceutically acceptable salts), and the biodegradable polymer(s) and one or more other active ingredients, surfactants, excipients or other ingredients or combinations thereof. When there are other active ingredients, surfactants, excipients or other ingredients or combinations thereof in the formulation, in some embodiments these other compounds or combinations thereof comprise less than 50 wt. %. less than 40 wt. %, less than 30 wt. %, less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
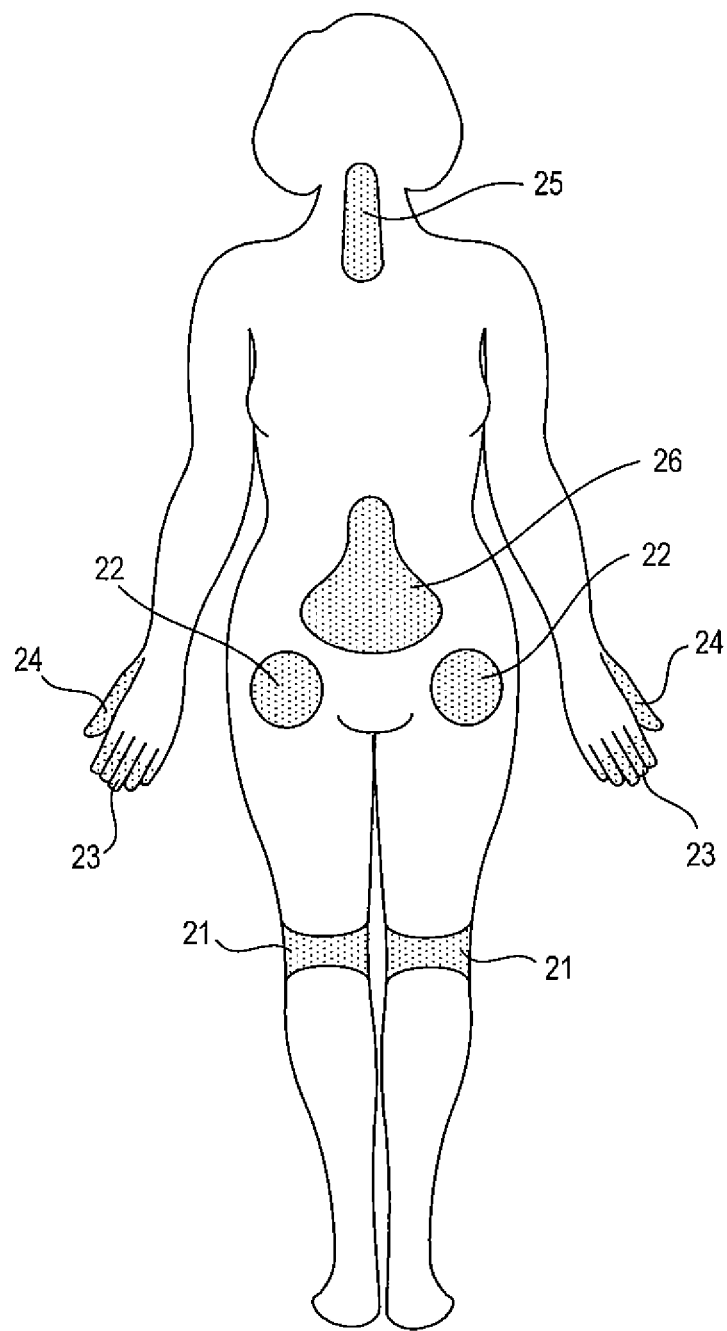
FIG. 1 illustrates a number of common locations within a patient that may be sites at which pain may occur and locations at which both the bupivacaine, and/or lidocaine immediate release formulation and the drug depot can locally be administered thereto and used to treat pain.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

DEFINITIONS

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

A "drug depot" is the composition in which the clonidine is administered to the body. Thus, a drug depot may comprise a physical structure to facilitate implantation and retention in a desired site (e.g., a disc space, a spinal canal, a tissue of the patient, particularly at or near a site of chronic pain, etc.). The drug depot may also comprise the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.01 cm to about 20 cm from the administration site and comprises clonidine. A drug depot may also include a pump or pellet.

A "therapeutically effective amount" or "effective amount" is such that when administered, the drug results in alteration of the biological activity, such as, for example, inhibition of inflammation, reduction or alleviation of pain or spasticity, improvement in the condition through muscle relaxation, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, etc.) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s). In some embodiments, the drug depot comprises a sustained release region or component that allows release of the clonidine over an extended period of time. In some embodiments, this is due to the drug eluting from the depot slowly. In some embodiments, the depot comprises from about 0.1% to about 30% by weight clonidine and 10% to 99.9% by weight of a polymer.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. Immediate release refers to the release of drug within a short time period following administration, e.g., generally within a few minutes to about 1 to 2 hours. In some embodiments, this is due to the drug eluting from the depot quickly. In another embodiment, it is due to the administration of the drug in a solution. In some embodiments, the drug depot comprises from about 10 wt % to about 99.9 wt % of bupivacaine or lidocaine, and 0.1% to about 80% by weight of a polymer.

The two types of formulations (sustain release and immediate release) may be used in conjunction. The sustained release and immediate release may be in one or more of the same depots. In various embodiments, the sustained release and immediate release may be part of separate depots. For example a bolus or immediate release formulation of bupivacaine, and/or lidocaine may be placed at or near the target site and a sustain release formulation of clonidine may also be placed at or near the same site. Thus, even after the bolus becomes completely accessible, the sustain release formulation would continue to provide the active ingredient for the intended tissue.

In various embodiments, the drug depot can be designed to cause an initial burst dose of therapeutic agent (e.g., bupivacaine, and/or lidocaine) within the first twenty-four to seventy-two hours after implantation. This can include within minutes to hours after the drug depot is implanted at the target tissue site. "Initial burst" or "burst effect" or "bolus dose" refers to the release of therapeutic agent (e.g., bupivacaine, and/or lidocaine) from the depot during the first twenty-four hours to seventy-two hours after the depot comes in contact with an aqueous fluid (e.g., synovial fluid, cerebral spinal fluid, etc.). In some embodiments, the bupivacaine, and/or lidocaine can also be administered in a separate bolus dose, before, during or after implanting the depot. The "burst effect" is believed to be due to the increased release of therapeutic agent (e.g., bupivacaine, and/or lidocaine) from the depot. In alternative embodiments, the depot (e.g., gel) is designed to avoid or reduce this initial burst effect (e.g., by applying an outer polymer coating to the depot). This can be so in the sustained release region of the depot or when the depot is designed for sustained release.

The burst effect may be an immediate release. The "burst effect" is believed to be due to the increased release of therapeutic agent (e.g., bupivacaine, and/or lidocaine) from the depot. The initial burst effect or bolus dose may be determined before hand by formulating the depot by calculating the quotient obtained by dividing (i) the effective amount by weight of therapeutic agent to be released from the depot or region in a predetermined initial period of time after implantation of the depot, by (ii) the total amount of therapeutic agent that is to be delivered from an implanted composition. It is understood that the initial burst may vary depending on the shape and surface area of the implant.

The burst effect with respect to the region or depot, in various embodiments, can be designed so that a larger initial dose may be released over a short period of time to achieve the desired effect. For example, if a drug depot is designed to release 100 mg of bupivacaine per 48 hours, then the initial burst dose or bolus dose region or depot will be designed to release a percentage of the dose within the first 24 hours (e.g., 50 mg of bupivacaine or 50% of the 48 hour dose within 24 hours). Thus, the burst effect of the drug depot or region releases more therapeutic agent than the sustained release region or depot.

In various embodiments, the drug depot may utilize an initial burst release of about 5% to about 15% of the total amount of the drug within 4 to 6 hours. In some embodiments, the drug depot may release 10% to about 25% through cumulative release of the drug within 24 hours. In some embodiments, 50% of the total cumulative dose released from the drug depot remains for approximately 60 days or more. In some embodiments, the drug depot may utilize an initial burst release from about 5% to about 10% of the amount of the drug in 24 hours or about 2 μg to about 40 μg in 24 hours. In various embodiments, the drug depot may utilize an initial burst release from about 5% to about 10% of the amount of the drug in 24 hours or about 5 μg to about 6 μg in 24 hours, then the drug depot may release 1 μg/day to about 20 μg/day at a constant release for about 50 days, then the amount released decreases 0.1 μg/day for approximately 70 days or more. In some embodiments, the drug depot may release about 50% of the total cumulative dose within 30 days to about 42 days and 70 days where under 80% of the drug releases. In various embodiments, the drug depot may utilize an initial burst release of about 5% to about 10% of the drug in 24 hours or 20 μg/24 hours to about 150 μg/24 hours then 5 μg/day up to 80 5 μg/day, constant release for 28 days or 30 days, then 28 to 50 days later the drug release decreases to 0.01 μg/day to about 5 μg/day past 70 days. In some embodiments, the drug depot releases 80% of the cumulative dose in 35 days and 20% over several months.

A region or depot that utilizes a burst effect or bolus dose will release more therapeutic agent (e.g., bupivacaine, and/or lidocaine) than the sustained release region or depot. For example, particularly with painful chronic conditions including rheumatoid arthritis, osteoarthritis, a spinal disc herniation (e.g., sciatica), carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, discogenic back pain, and joint pain or the like, the initial burst effect of the drug depot or region of the drug depot will be advantageous as it will provide more immediate pain relief as a bolus dose of drug will be released at or near the target tissue site and provide the desired reducing, or alleviation of signs or symptoms of pain and/or inflammation. For example, the drug depot or region of the drug depot may release 51%, 52%, 53%, 54%, 55%, % 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% or up to 10,000% of the daily dose within the first one to twelve hours to reduce, prevent or treat pain. In some embodiments, the immediate release region of the depot may release a bolus dose of bupivacaine, and/or lidocaine that is from about 0.1 mg to about 500 mg.

"Treating" or "treatment" of a disease or condition refers to executing a protocol that may include administering one or more drugs to a patient (human, other normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition. In addition, treating or treatment does not require complete alleviation of signs or symptoms, does not require a cure, and specifically includes protocols that have only a marginal effect on the patient. "Reducing pain and/or inflammation" includes a decrease in pain and/or inflammation and does not require complete alleviation of pain and/or inflammation signs or symptoms, and does not require a cure. In various embodiments, reducing pain and/or inflammation includes even a marginal decrease in pain and/or inflammation. By way of example, the administration of the effective dosage of clonidine may be used to prevent, treat or relieve the symptoms of pain and/or inflammation for different diseases or conditions. These disease/conditions may comprise oral-facial diseases, bursitis, tendonitis, chronic inflammatory diseases, including, but not limited to autoimmune diseases, such as multiple sclerosis, rheumatoid arthritis, osteoarthritis, insulin dependent diabetes (type I diabetes), systemic lupus erythrematosis and psoriasis, immune pathologies induced by infectious agents, such as helminthic (e.g., leishmaniasis) and certain viral infections, including HIV, and bacterial infections, including Lyme disease, tuberculosis and lepromatous leprosy, tissue transplant rejection, graft versus host disease and atopic conditions, such as asthma and allergy, including allergic rhinitis, gastrointestinal allergies, including food allergies, eosinophilia, conjunctivitis or glomerular nephritis.

One chronic condition is sciatica. In general, sciatica is an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area. In various embodiments, the clonidine may be used to reduce, treat, or prevent sciatic pain and/or inflammation by locally administering the clonidine at one or more target tissue sites (e.g., nerve root, dorsal root ganglion, focal sites of pain, at or near the spinal column, etc.).

In some embodiments, the drug depot can be used to treat one or more target tissue sites that are involved in conditions/diseases, such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, a surgical wound site or an incision site or the like.

The term "implantable" as utilized herein refers to a biocompatible device (e.g., drug depot) retaining potential for successful placement within a mammal. The expression "implantable device" and expressions of the like import as utilized herein refers to an object implantable through surgery, injection, or other suitable means whose primary function is achieved either through its physical presence or mechanical properties.

"Localized" delivery includes delivery where one or more drugs are deposited within a tissue, for example, a nerve root of the nervous system or a region of the brain, or in close proximity (within about 0.1 cm, or preferably within about 10 cm, for example) thereto. For example, the drug dose delivered locally from the drug depot may be, for example, 10%, 20%, 30%, 40%, 50%, 60%, 70%, 80%, 90%, 95%, 99%, or 99.9% less or as low as 99.999% than the oral dosage or injectable dose. In turn, systemic side effects, such as for example, liver transaminase elevations, hepatitis, liver failure, myopathy, constipation, etc. may be reduced or eliminated.

The term "mammal" refers to organisms from the taxonomy class "mammalian," including but not limited to humans, other primates such as chimpanzees, apes, orangutans and monkeys, rats, mice, cats, dogs, cows, horses, etc.

The phrase "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

The phrase "release rate profile" refers to the percentage of active ingredient that is released over fixed units of time, e.g., mcg/hr, mcg/day, 10% per day for ten days in an in vivo or in vitro system, etc. As persons of ordinary skill know, a release rate profile may, but need not, be linear. By way of a non-limiting example, the drug depot may be a ribbon-like fiber that releases the clonidine over a period of time.

The term "solid" is intended to mean a rigid material, while, "semi-solid" is intended to mean a material that has some degree of flexibility, thereby allowing the depot to bend and conform to the surrounding tissue requirements.

"Targeted delivery system" provides delivery of one or more drugs depots, gels or depots dispersed in the gel having a quantity of therapeutic agent that can be deposited at or near the target site as needed for treatment of pain, inflammation or other disease or condition.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "G" refers to polyglycolide.

The abbreviation "PEG" refers to poly(ethylene glycol).

The abbreviation "PLGA" refers to poly(lactide-co-glycolide) also known as poly(lactic-co-glycolic acid), which are used interchangeably.

The abbreviation "PLA" refers to polylactide.

The abbreviation "POE" refers to poly(orthoester).

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Clonidine

When referring to clonidine, unless otherwise specified or apparent from context it is understood that the inventors are also referring to pharmaceutically acceptable salts. One well-known commercially available salt for clonidine is its hydrochloride salt. Some other examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like.

Further, when referring to clonidine and other active ingredients, they may not only be in the salt form, but also in the base form (e.g., free base). In various embodiments, if it is in the base form, it may be combined with polymers under conditions in which there is not severe polymer degradation, as may be seen upon heat or solvent processing that may occur with PLGA or PLA. By way of a non limiting example, when formulating clonidine with poly(orthoesters) it may be desirable to use the clonidine base formulation. By contrast, when formulating clonidine with PLGA, it may be desirable to use the HCl salt form. In some embodiments, the clonidine may be incorporated into a polymer core with a polymer and then coated with the same or different polymer.

Pharmaceutically acceptable salts of clonidine include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, eg., fatty acid salts having greater than 2 carbons, greater than 8 carbons or greater than 16 carbons, such as butyric, caprioc, caprylic, capric, lauric, mystiric, palmitic, stearic, arachidic or the like.

In some embodiments, in order to reduce the solubility of the clonidine to assist in obtaining a controlled release depot effect, clonidine is utilized as the free base or utilized in a salt which has relatively lower solubility. For example, the present application can utilize an insoluble salt such as a fatty acid salt. Representative fatty acid salts include salts of oleic acid or linoleic acid. In preferred embodiments fatty acid salts with between 8 to 20 carbons are used to produce salts with low solubility, such as clonidine palmeate and clonidine stearate. Most preferably, fatty acid salts with between 12 to 18 carbons are used. Other embodiments can utilize a lipid soluble salt of clonidine.

Suitable clonidine depots for use in the present application are described in U.S. Ser. No. 12/420,197, filed Apr. 8, 2009 and published as US20090264490. The entire disclosure is herein incorporated by reference.

In some embodiments, the clonidine has a drug load of 3% to 18% by weight based on the total weight of the device. In some embodiments, the clonidine is disposed in a polymer of PLA having an inherent viscosity of 0.45-0.55 and having an ester end group, or the clonidine is disposed in a polymer of PLA having an inherent viscosity of 0.60-0.80 and having an ester end group. In some embodiments, the drug depot comprises a pellet having a diameter of 0.5 mm diameter or a 0.75 mm diameter.

In some embodiments, the drug depot has a modulus of elasticity in the range of about $1 \times 10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$. In some embodiments, the drug depot is in the form of a solid. In some embodiments, the drug depot comprises of clonidine, bupivacaine and lidocaine.

The clonidine or its pharmaceutically acceptable salt may be administered with a muscle relaxant. Exemplary muscle relaxants include by way of example and not limitation, alcuronium chloride, atracurium bescylate, carbamate, carbolonium, carisoprodol, chlorphenesin, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

In some embodiments, the clonidine can be in powdered form having a particle sizes predominantly in a range from about 3.5 to about 10 micrometers that can be reconstituted for delivery.

The drug depot may comprise other therapeutic agents in addition to the clonidine as well. These therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as glucocorticoids, antioxidants, such as dithiocarbamate, and other compounds, such as, for example, sulfasalazine.

Examples of therapeutic agents suitable for use also include, but are not limited to an anti-inflammatory agent, an analgesic agent, or an osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine[2-hydroxy-5-[-4-[C2-pyridinylamino)sulfonyl]azo]benzoic acid, sulindac, tepoxalin or tolmetin; as well as antioxidants, such as dithiocarbamate, steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor (e.g., GDF-5), a LIM mineralization protein, CDMP or progenitor cells or a combination thereof.

Suitable analgesic agents include, but are not limited to, acetaminophen, bupivacaine, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

The therapeutic agent in the device may include, but is not limited to, members of the fibroblast growth factor family, including acidic and basic fibroblast growth factor (FGF-1 and FGF-2) and FGF-4, members of the platelet-derived growth factor (PDGF) family, including PDGF-AB, PDGF-BB and PDGF-AA; EGFs; the TGF-β superfamily, including TGF-β1, 2 or 3; osteoid-inducing factor (OIF); angiogenin(s); endothelins; hepatocyte growth factor or keratinocyte growth factor; members of the bone morphogenic proteins (BMP's) BMP-1, BMP-3, BMP-2; OP-1, BMP-2A, BMP-2B, or BMP-7; HBGF-1 or HBGF-2; growth differentiation factors (GDF's); members of the hedgehog family of proteins, including indian, sonic and desert hedgehog; ADMP-1; other members of the interleukin (IL) family; or members of the colony-stimulating factor (CSF) family, including CSF-1, G-CSF, and GM-CSF, or isoforms thereof; or VEGF, NELL-1 (neural epidermal growth factor-like 1), CD-RAP (cartilage-derived retinoic acid-sensitive protein) or combinations thereof.

In some embodiments, the device comprises osteogenic proteins. Exemplary osteogenic proteins include, but are not limited to, OP-1, OP-2, OP-3, BMP-2, BMP-3, BMP-3b, BMP-4, BMP-5, BMP-6, BMP-9, BMP-10, BMP-11, BMP-12, BMP-13, BMP-14, BMP-15, GDF-1, GDF-2, GDF-3, GDF-5, GDF-6, GDF-7, GDF-8, GDF-9, GDF-10, GDF-11, GDF-12, CDMP-1, CDMP-2, CDMP-3, DPP, Vg-1, Vgr-1, 60A protein, NODAL, UNIVIN, SCREW, ADMP, NEURAL, and TGF-beta. As used herein, the terms "morphogen," "bone morphogen," "BMP," "osteogenic protein" and "osteogenic factor" embrace the class of proteins typified by human osteogenic protein 1 (hOP-1).

Exemplary growth factors include, but are not limited to, members of the transforming growth factor beta family, including bone morphogenetic protein 2 (BMP-2); bone morphogenetic protein 4 (BMP-4); and transforming growth factors beta-1, beta-2, and beta-3 (potent keratinocyte growth factors). Other useful members of the transforming growth factor beta family include BMP-3, BMP-5, BMP-6, BMP-9, DPP, Vg1, Vgr, 60A protein, GDF-1, GDF-3, GDF-5, GDF-6, GDF-7, CDMP-1, CDMP-2, CDMP-3, BMP-10, BMP-11, BMP-13, BMP-15, Univin, Nodal, Screw, ADMP, Neural, and amino acid sequence variants thereof. Other growth factors include epidermal growth factor (EGF), which induces proliferation of both mesodermal and ectodermal cells, particularly keratinocytes and fibroblasts; platelet-derived growth factor (PDGF), which exerts proliferative effects on mesenchymal cells; fibroblast growth factor (FGF), both acidic and basic; and insulin-like growth factor 1 (IGF-1) or 2 (IGF-2), which mediate the response to growth hormone, particularly in bone growth. Further growth factors include osteogenic proteins. A particularly preferred osteogenic protein is OP-1, also known as bone morphogenetic protein 7 (BMP-7). OP-1 is a member of the transforming growth factor beta gene superfamily.

Bupivacaine or Lidocaine

In some embodiments, the drug depot comprises bupivacaine and/or lidocaine in an immediate release region or layer of the depot that is released in a bolus dose as the polymer degrades.

When referring to bupivacaine or lidocaine, unless otherwise specified or apparent from context it is understood that the inventors are also referring to pharmaceutically acceptable salts. Some examples of potentially pharmaceutically acceptable salts include those salt-forming acids and bases that do not substantially increase the toxicity of the compound. Some examples of these salts include salts of alkali metals such as magnesium, potassium and ammonium. Salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like. To the extent these salts of bupivacaine can be created for safe administration to a mammal, they are within the scope of the present invention.

In some embodiments, the bupivacaine is in base form or is in a salt form such as bupivacaine hydrochloride. In some embodiments, the lidocaine is in base form or is in salt form such as lidocaine hydrochloride. In some embodiments, the lidocaine comprises acetamide 2-(diethylamino)-N-(2,6-dimethylphenyl).

In some embodiments, the clonidine is first compounded with a polymer to make a first component of the drug depot. In this first component, the clonidine may for example, comprise 2.5% to 18% by weight. The bupivacaine or lidocaine may separately be compounded with a polymer to make a second component of the drug depot. In this second component, the bupivacaine or lidocaine may for example comprise 50%-70% by weight. In some embodiments, the percentage of clonidine to bupivacaine or lidocaine is between about 1:30, 1:25, 1:20, 1:15, 1:12.5, 1:11, 1:10, 1:9, 1:8, 1:7, 1:6, 1:5, 1:4, 1:3, 1:2, or 1:1. The bupivacaine or lidocaine and clonidine may also be formulated together with one polymer. Thus, a combination product comprising clonidine and bupivacaine may by way of example be formed by combining these active ingredients with a polymer as part of one formulation to generate a combination drug product. By way of another example, each active formulation is separately developed for co-administration to a site, e.g., a surgical wound site.

In some embodiments, the bupivacaine or lidocaine can be released from the depot after implantation and over a period of 2 to 14 days. In some embodiments, the drug depot releases from the immediate release region a bolus dose of bupivacaine or lidocaine at a dose of from about 10 mg to about 500 mg over a period of one to 6 hours to treat pain. The release may be over 1 day to 14 days.

In some embodiments, the drug depot releases about 1 mg to 30 mg/day of bupivacaine or lidocaine for 1 to 10 days or 1 day to 14 days. In some embodiments it releases 20 to 360 mg/day or 40 to 120 mg/day or 80 to 180 mg/day or 120 to 240 mg/day or 160 to 300 mg/day or 200 to 360 mg/day of bupivacaine or lidocaine. This dose is often much lower than the dose used to provide nerve block in surgery.

In some embodiments, the therapeutically effective dosage amount and the release rate profile are sufficient to treat the pain or disease or condition for a period of 3-12 days; in other embodiments the release rate profile is sufficient to treat pain for a period of 7-10 days.

In some embodiments of the present application, the drug depot may release 5%, 10%, 15%, 20%, 25%, 30%, 40%, 50%, 60%, 70%, 80%, 90%, 95%, or 99% of the bupivacaine or lidocaine and clonidine relative to a total amount of bupivacaine or lidocaine and clonidine loaded in the drug depot over a period of 3 to 12 days after the drug depot is administered to the target tissue site.

In other embodiments, it may be advantageous for there to be a greater release of the bupivacaine or lidocaine at a time right after the depot is implanted, i.e., a burst effect for the bupivacaine or lidocaine and either no burst effect for the clonidine or a relatively smaller burst effect for the clonidine relative to the bupivacaine or lidocaine. Thus, in some embodiments, there may be a release profile of the bupivacaine or lidocaine that releases a first percentage of the bupivacaine or lidocaine relative to the total amount of bupivacaine or lidocaine over the first two days and a release profile of the clonidine that releases a first percentage of the clonidine relative to the total amount of the clonidine over the first two days. The percentage of clonidine released over those first two days may be less than the percentage of bupivacaine or lidocaine released over those first two days. Thus, in some embodiments, more than 30 percent of the bupivacaine or lidocaine is released in the first two days and less than 25 percent of the clonidine is released in that time period. In some embodiments, more than 40 percent of the bupivacaine or lidocaine is released in the first two days and less than 35 percent of the clonidine is released in that time period. In some embodiments, more than 50 percent of the bupivacaine or lidocaine is released in the first two days and less than 45 percent of the clonidine is released in that time period.

In some embodiments, the bupivacaine load is about 0.25% to about 0.75% by weight based on the total weight of the drug depot. In some embodiments, the lidocaine load is about 1% to about 2% by weight based on the total weight of the drug depot.

Other exemplary depots and release profiles for bupivacaine and clonidine are described in U.S. Ser. No. 12/423,201, filed Apr. 14, 2009 and published as US20100203102 and U.S. Ser. No. 12/420,110, filed Apr. 8, 2009 and published as US20090263321, the contents of which are incorporated by reference herein.

In some embodiments of the present application, the drug depot releases 5 mg to 60 mg of bupivacaine or lidocaine and 10 μg to 100 μg of clonidine every 4 to 6 hours to treat pain or inflammation over a span of 3 to 12 days or 5 to 10 days.

The clonidine, bupivacaine and/or lidocaine may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the depot will be a solid or semi-solid formulation comprised of a biocompatible material that can be biodegradable.

Exemplary excipients that may be formulated with clonidine, bupivacaine and/or lidocaine in addition to the biodegradable polymer include but are not limited to MgO (e.g., 1 wt. %), 5050 DLG 6E (Lakeshore Biomaterials, Birmingham, Ala.), 5050 DLG 1A (Lakeshore Biomaterials, Birmingham, Ala.), mPEG, TBO-Ac, mPEG, Span-65, Span-85, pluronic F127, TBO-Ac, sorbitol, cyclodextrin, maltodextrin, pluronic F68, CaCl, 5050 DLG-7A (Lakeshore Biomaterials, Birmingham, Ala.) and combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.001 wt. % to about 10 wt. % of the formulation. In some embodiments, the excipients comprise from about 0.001 wt. % to about 50 wt. % of the formulation. In some embodiments, the excipients comprise from about 0.001 wt. % to about 2 wt. % of the formulation.

In some embodiments, the polymer can be in powdered form having a particle size predominantly in a range from about 3.5 to about 10 micrometers that can be reconstituted for delivery.

In various embodiments, the non-active ingredients will be durable within the tissue site for a period of time equal to or greater than (for biodegradable components) or greater than (for non-biodegradable components) the planned period of drug delivery.

In some embodiments, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s). Non-biodegradable polymers include but are not limited to PVC and polyurethane.

In some embodiments, the drug depot may not be fully biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics, methacrylates, poly(N-isopropylacrylamide), PEO-PPO-PEO (pluronics) or combinations thereof. Typically, these types of drug depots may need to be removed after a certain amount of time.

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bioerodible, a bioabsorbable, and/or a biodegradable biopolymer that may provide immediate release, or sustained release of the clonidine, bupivacaine and/or lidocaine. Examples of suitable sustained release biopolymers include but are not limited to poly(alpha-hydroxy acids), poly (lactide-co-glycolide) (PLGA), polylactide (PLA), polyglycolide (PG), polyethylene glycol (PEG) conjugates of poly(alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations. In some embodiments, these biopolymers may also be coated on the drug depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the drug from the depot. In some embodiments, the range of the coating on the drug depot ranges from about 5 microns to about 250 microns or 5 microns to about 200 microns to delay release from the drug depot.

In some embodiments, the plasticizer is used to lower glass translation temperature in order to affect stability of the drug depot.

In various embodiments, the drug depot comprises poly (lactide-co-glycolide) (PLGA), polylactide (PLA), polyglycolide (PGA), D-lactide, D,L-lactide, L-lactide, D,L-lactide-co-ϵ-caprolactone, L-lactide-co-ϵ-caprolactone, D,L-lactide-co-glycolide-co-ϵ-caprolactone or a combination thereof.

In some embodiments, the drug depot comprises one or more polymers (e.g., PLA, PLGA, etc.) having a MW of from about 15,000 to about 150,000 Da or from about 25,000 to about 100,000 Da.

In some embodiments, the drug depot comprises one or more polymers (e.g., poly(D-lactide-co-caprolactone, etc.) having an inherent viscosity of 0.6 to about 1.0 dL/gm and a MW of 50,000 to about 125,000 Da.

In some embodiments, the clonidine, bupivacaine and/or lidocaine is administered in a depot that is solid or in semi-solid form. The solid or semi-solid form of the depot may have a pre-dosed viscosity in the range of about 1 to about 2000 centipoise (cps), 1 to about 200 cps, or 1 to about 100 cps. After the solid or semi-solid depot is administered to the target site, the viscosity of the semi-solid or solid depot will increase and the semi-solid will have a modulus of elasticity in the range of about $1 \times -10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In various embodiments, the semi-solid or solid depot may comprise a polymer having a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

As persons of ordinary skill in the art are aware, an implantable depot compositions having a blend of polymers with different end groups are used the resulting formulation will have a lower burst index and a regulated duration of delivery. For example, one may use polymers with acid (e.g., carboxylic acid) and ester end groups (e.g., methyl or ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower initial burst and a regulated duration of delivery.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the depot is to be placed in the spinal area, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film or sheet (e.g., ribbon-like) or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 4 mm. In various embodiments, as the diameter decreases, the surface area that comes in contact with the bodily fluid of the depot increases and therefore release of the drug from the depot increases. In various embodiments, the drug depot may have a layer thickness of from about 0.005 to 1.0 mm, such as, for example, from 0.05 to 0.75 mm.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, bismuth, iodine, tantalum, tungsten, and/or metal beads or particles. In various embodiments, the radiographic marker could be a spherical shape or a ring around the depot.

FIG. 1 illustrates a number of common locations within a patient that may be sites at which pain can occur and at which the clonidine depot and the injectable bupivacaine and/or lidocaine may be administered. It will be recognized that the locations illustrated in FIG. 1 are merely exemplary of the many different locations at which pain can occur. For example, pain relief may be required at a patient's knees 21, hips 22, fingers 23, thumbs 24, neck 25, and spine 26.

Gel

In various embodiments, the clonidine, bupivacaine and/or lidocaine is administered in a gel. The gel may have a pre-dosed viscosity in the range of about 1 to about 2000 centipoise (cps), 1 to about 200 cps, or 1 to about 100 cps. After the gel is administered to the target site, the viscosity of the gel will increase and the gel will have a modulus of elasticity (Young's modulus) in the range of about $1 \times -10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, a depot comprises an adherent gel comprising clonidine bupivacaine and/or lidocaine that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1 \times -10^2$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening gels (after delivery) may have a rubbery consistency and have a modulus of elasticity in the range of about $1 \times -10^2$ to about $2 \times 10^6$ dynes/cm$^2$, or $1 \times 10^5$ to about $7 \times 10^5$ dynes/cm$^2$, or $2 \times 10^5$ to about $5 \times 10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polymer comprises 20 wt. % to 90 wt. % of the formulation.

In various embodiments, the molecular weight of the gel can be varied by many methods known in the art. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, incorporation of chain transfer or chain capping agents and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition that includes a low-molecular weight polymer. Polymeric gel formulations that include high molecular weight polymers, also tend to have a higher solution viscosity than a polymeric gel that includes low-molecular weight polymers. In various embodiments, the molecular weight of the polymer can be a wide range of values. The average molecular weight of the polymer can be from about 1000 Da to about 10,000,000 Da; or about 1,000 Da to about 1,000,000 Da; or about 5,000 Da to about 500,000 Da; or about 10,000 Da to about 100,000 Da; or about 20,000 Da to 50,000 Da.

When the gel is designed to be a flowable gel, it can vary from low viscosity, similar to that of water, to high viscosity, similar to that of a paste, depending on the molecular weight and concentration of the polymer used in the gel. The viscosity of the gel can be varied such that the polymeric composition can be applied to a patient's tissues by any convenient technique, for example, by brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and may have a longer degradation time). Typically, when the polymers have similar components but different MWs, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, and about 1.8 to about 2.1 dL/g.

In some embodiments, when the polymer materials have different chemistries (e.g., high MW DLG 5050 and low MW DL), the high MW polymer may degrade faster than the low MW polymer.

In various embodiments, the polymer may have a pre-dosed viscosity in the range of about 1 to about 2000 centipoise (cps), 1 to about 200 cps, or 1 to about 100 cps. The depot may have a modulus of elasticity in the range of about $1 \times 10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In various embodiments, the polymer has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, about 0.80 to about 1.00 dL/g, about 0.90 to about 1.10, about 1.0 to about 1.2, about 1.1 to about 1.3, about 1.2 to about 1.4, about 1.3 to about 1.5, about 1.4 to about 1.6, about 1.5 to about 1.7, about 1.6 to about 1.8, about 1.7 to about 1.9, and about 1.8 to about 2.1.

In various embodiments, the gel can have a viscosity of about 300 to about 5,000 centipoise (cp). In other embodiments, the gel can have a viscosity of from about 5 to about 300 cps, from about 10 cps to about 50 cps, or from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly(acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly (N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the gel, microspheres may be dispersed within the gel, the microspheres being loaded with clonidine. In one embodiment, the microspheres provide for a sustained release of the clonidine. In yet another embodiment, the gel, which is biodegradable, prevents the microspheres from releasing the clonidine; the microspheres thus do not release the clonidine until they have been released from the gel. For example, a gel may be deployed around a target tissue site (e.g., a nerve root). Dispersed within the gel may be a plurality of microspheres that encapsulate the desired therapeutic agent. Certain of these microspheres degrade once released from the gel, thus releasing the clonidine.

Microspheres, much like a fluid, may disperse relatively quickly, depending upon the surrounding tissue type, and hence disperse the clonidine, bupivacaine and/or lidocaine. In some situations, this may be desirable; in others, it may be more desirable to keep the clonidine tightly constrained to a well-defined target site. The present invention also contemplates the use of adherent gels to so constrain dispersal of the therapeutic agent. These gels may be deployed, for example, in a disc space, in a spinal canal, or in surrounding tissue.

Drug Delivery

It will be appreciated by those with skill in the art that the depot can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 15 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655 (mm). The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

In various embodiments, a kit is provided that may include additional parts along with the drug depot and/or medical device combined together to be used to implant the drug depot. The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may include an agent for radiographic imaging or one or more bolus doses of bupivacaine, lidocaine, steroid, and or clonidine. Each tool may be separately packaged in a plastic pouch that is radiation sterilized. A cover of the kit may include illustrations of the implanting procedure and a clear plastic cover may be placed over the compartments to maintain sterility.

In some embodiments, a kit is provided with instruction to use an injectable drug from another kit.

In various embodiments, there is a kit comprising a plurality of implantable drug depots useful for reducing, preventing or treating pain in a patient in need of such treatment, the kit comprising a first set of the plurality of drug depots comprising a biodegradable polymer capable of releasing a therapeutically effective bolus dose of bupivacaine and/or lidocaine at a site beneath the skin and a second set of the plurality of drug depots comprising a second biodegradable polymer capable of providing sustained release of a therapeutically effective amount of the clonidine over a period of at least three days.

In various embodiments, a method for delivering a therapeutic agent into a site of a patient is provided, the method comprising inserting a cannula at or near a target tissue site and implanting the drug depot at the target site beneath the skin of the patient and brushing, dripping, injecting, or painting the gel in the target site to hold or have the drug depot adhere to the target site. In this way unwanted migration of the drug depot away from the target site is reduced or eliminated.

In various embodiments, to administer the gel having the drug depot dispersed therein to the desired site, first the cannula or needle can be inserted through the skin and soft tissue down to the target tissue site and the gel administered at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required, a subsequent layer or layers of gel can be applied on the drug depot to surround the depot and further hold it in place. Alternatively, the drug depot may be implanted first and then the gel placed around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

In various embodiments, when the target site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

Injectable Bupivacaine and Lidocaine Formulation

The bupivacaine and/or lidocaine formulation may be designed to provide immediate relief from pain and in some embodiments may be injected. For example, the bupivacaine and/or lidocaine formulation may be an epidural or intrathecal liquid injection.

When the liquid formulation comprises bupivacaine, the bupivacaine can be in powdered form having a particle sizes predominantly in a range from about 3.5 to about 10 micrometers that can be reconstituted for delivery. In some embodiments, the bupivacaine can be given as a local bolus dose before, during or after implanting the drug depot. For example, the bupivacaine can be given at or near the target tissue site from a 0.125% or 0.5% solution that can be preservative free at a dose of from about 10 mg to about 500 mg or 12.5 mg to 50 mg. The bupivacaine can have a pH adjusted to a range between pH 5.0 to 7.5. The osmolality of the solution can be between 275-300 mOsm/kg. In some embodiments, the bupivacaine can be bupivacaine hydrochloride.

When the liquid formulation comprises lidocaine, the lidocaine suitable for use in the present application is commercially available from various manufacturers, for example, from DSM Wyckoff, South Haven, Mich., and packaged by Cardinal Health Technologies-STW, Woodstock, Ill., as 1% or 4% lidocaine solution for intravenous use or epidural use. Lidocaine can be in solution form and administered as a single bolus dose in a suitable diluent, for example, normal or diluted saline solution, having a pH adjusted to a range between pH 5.0 to 7.5. The osmolality of the solution can be between 275-300 mOsm/kg.

The lidocaine can be in powdered form having a particle sizes predominantly in a range from about 3.5 to about 10 micrometers that can be reconstituted for delivery. In some embodiments, the lidocaine can be given as a local bolus dose before, during or after implanting the drug depot. For example, the lidocaine can be given at or near the target tissue site from a 0.5%, 1%, 2%, 5% solution that can be preservative free at a dose of from about 10 mg to about 500 mg. In some embodiments, the lidocaine can be lidocaine hydrochloride or lidocaine hydrocarbonate.

Determination of the effective dosage of administered bupivacaine, lidocaine, and/or clonidine and the regimen used for treatment of each patient depends on the responsiveness of the individual patient to the treatment.

The unit dose vial for the application of a liquid formulation containing bupivacaine and/or lidocaine preferably contains enough bupivacaine and/or lidocaine to be therapeutically effective for a human, and the indication to be treated can be any suitable condition. In certain preferred applications, the single unit dose vial or preloaded syringe of the pharmaceutical composition of the invention is suitable for use in administering the composition to either the cerebrospinal system, or to the musculoskeletal system. The pharmaceutical composition may be administered in a total volume of about 10 microliters to about 2 ml, preferably about 100 microliters to about 1 ml. The dose may also have a total volume of about 50 microliters or less. The dose may preferably have a total volume of or up to about 10 microliters, 15 microliters, 20 microliters, 25 microliters, 30 microliters, 35 microliters, 40 microliters, 45 microliters, 50 microliters, 55 microliters, 60 microliters, 65 microliters, 70 microliters, 75 microliters, 80 microliters, 85 microliters, 90 microliters, 95 microliters, 100 microliters, 200 microliters, 300 microliters, 400 microliters, 500 microliters, 600 microliters, 700 microliters, 800 microliters, 900 microliters, or 1 ml or intermediate dosages. The dose may have a total volume greater than 1 ml, such as 1.1 ml, 1.2 ml, 1.3 ml, 1.4 ml, 1.5 ml, 1.6 ml, 1.7 ml, 1.8 ml, 1.9 ml, 2 ml, or more than about 2 ml, as well as intermediate dosages. The pharmaceutical composition is preferably administered in a single injection or, alternatively and less preferably, in multiple injections, wherein multiple unit doses may be administered to the patient at the discretion of the treating physician based on the patient's size, medical condition, or other relevant criteria in determining the appropriate dosage. Preferably, a patient will receive a single dose of clonidine. In some cases, a patient may receive multiple doses in a single treatment. In some embodiments, the clonidine may be administered within four hours before, during, or after implanting the drug depot or within 5 minutes, within 10 minutes, within 15 minutes, within 20 minutes, within 25 minutes, within 30 minutes, within 35 minutes, within 40 minutes, within 45 minutes, within 50 minutes, within 55 minutes, or within 60 minutes of implanting the drug depot.

According to some embodiments, only a single dose of bupivacaine and/or lidocaine is given. According to other embodiments, multiple doses of the bupivacaine and/or lidocaine may be given. When multiple doses are give, they may for example, be given over about 1 to about 24 hours or about 1 to about 2 hours, or about 2 hours to about 3 hours, or about 3 hours to about 4 hours, or about 4 hours to about 5 hours or about 5 hours to about 6 hours or about 6 hours to about 7 hours or about 7 hours to about 8 hours or about 8 hours to about 9 hours or about 9 hours to about 10 hours or about 10 hours to about 11 hours or about 11 hours to about 12 hours or about 12 hours to about 13 hours or about 13 hours to about 14 hours or about 14 hours to about 15 hours or about 15 hours to about 16 hours or about 16 hours to about 17 hours or about 17 hours to about 18 hours or about 18 hours to about 19 hours or about 19 hours to about 20 hours or about 20 hours to about 21 hours or about 21 hours to about 22 hours or about 22 hours to about 23 hours or about 23 hours to about 24 hours.

In some embodiments, the bupivacaine and/or lidocaine formulation is free from classical preservatives and/or free of dispersion agents. In some embodiments, the bupivacaine and/or lidocaine formulation comprises, consists of or consists essentially of the active ingredient (or its pharmaceutically acceptable salt), water and optionally a suitable excipient.

Exemplary excipients for the bupivacaine and/or lidocaine injection formulation include but are not limited to methylcellulose, hydroxypropylmethylcellulose, hydroxyethylcellulose, polyvinyl alcohol, mannitol, trehalose and polyethylene glycol. In some embodiments, the clonidine formulation may for example contain a minimum excipient concentration of at least about 0.2%, or at least about 0.35%, or at least about 0.5%, wherein the percentages are measured in weight per volume. Additionally, in some embodiments, the clonidine formulation may contains a maximum excipient, pore-former or plasticizer concentration of about 5%, or about 2%, or about 1% excipient, wherein these percentages are measured in weight per volume.

In some embodiments, when the active ingredient in the liquid formulation is a bupivacaine and/or lidocaine, the bupivacaine and/or lidocaine and excipient may be carried by an aqueous carrier, which may be a combination of a salt and water. Any suitable salt can be employed; however, the salt should be acceptable for pharmaceutical use in the concentration employed and is more preferably suitable for cerebral spinal systems and/or musculoskeletal use in the concentration employed. The salt may for example be sodium chloride. The pharmaceutical composition preferably contains at least about 0.7% (w/v) sodium chloride and no more than about 1.1% (w/v) sodium chloride (e.g., about 0.8-1% (w/v)). More preferably, the pharmaceutical composition contains about 0.9% sodium chloride. Additionally, the salt concentration or excipient concentration or both are preferably adjusted, if necessary, to provide an osmolarity of from about 200 mOsm to about 400 mOsm.

In some embodiments, the active ingredient (e.g., bupivacaine and/or lidocaine, etc.) may be in powder form and can be reconstituted with one or more liquid diluents that may be aqueous. For example, an aqueous liquid diluent may be water, pharmaceutically acceptable aqueous solutions, aqueous saline solutions (NS, ½ NS, etc.), Ringer's solutions, lactated Ringer's solutions, bicarbonate solutions, or aqueous dextrose solutions, or combinations thereof. The liquid diluent may contain one or more excipients such as the antioxidant BHT (butylated hydroxytoluene).

In another embodiment, the liquid diluent is non-aqueous and comprises one or more surfactants, e.g., non-ionic surfactants. In general, the weight to weight ratio (w/w) between the active ingredient or a salt thereof and the non-ionic surfactant(s) may be from about 1:10,000 to about 1:1. Useful non-ionic surfactants can include a polyethoxylated castor oil, a polysorbate, a sorbitan ester, a polyoxyethylene fatty acid ester, a polyoxyethylene fatty acid ether, a polyoxyethylene alkyl ether, and an ethoxylated fatty acid.

In other embodiments, a liquid diluent may be a combination of aqueous diluents and non-aqueous diluents. For example, a non-aqueous liquid diluent comprising one or more non-ionic surfactants may further include an aqueous diluent, such as water, pharmaceutically acceptable aqueous solutions, aqueous saline solutions, Ringer's solutions, lactated Ringer's solutions, bicarbonate solutions, aqueous dextrose solutions, or combinations thereof. In a specific embodiment, the volume to volume ratio (v/v) of non-ionic surfactant to aqueous diluent may be from about 100:1 to about 1:20,000.

When the liquid formulation comprises both the bupivacaine and/or lidocaine and the clonidine depot mixed in it, all or a fraction of each of the above-described formulation may be combined in the same syringe or co-administered through different syringes. In some embodiments, a steroid can be given, before, during or after the analgesic (bupivacaine and/or lidocaine) is given and the drug depot.

Timing of Introduction

In certain embodiments, first the bupivacaine and/or lidocaine formulation is introduced into body of the patient at or near the target site and next the drug depot (containing long acting clonidine) is administered or vice versa. The bupivacaine and/or lidocaine formulation may be designed to provide immediate release upon administration. The drug depot may be part of a formulation that is designed to provide both immediate release and sustained release capabilities or it may be part of a formulation that is designed to provide only a sustained release.

Moreover, depending upon the formulation of the drug depot, the sustained release profile may begin after a certain amount of time, e.g., after the time at with the active ingredients from the bupivacaine and/or lidocaine formulation no longer provide the desired result or shortly before they will no longer provide the desired result. For example, if the injectable bupivacaine and/or lidocaine formulation provides effective pain release for 24 hours, the drug depot formulation may be designed to begin its release at the same time the injectable formulation is introduced, after about two hours, after about four hours, after about six hours, after about eight hours, after about ten hours, after about twelve hours, after about fourteen hours, after about sixteen hours, after about eighteen hours, after about twenty hours, after about twenty-two hours or at about twenty-four hours.

The timing of the release of the active ingredient may also be designed to be dependant on the percentage of duration of the effect of the active ingredient. For example, the drug depot may be formulated to begin its release immediately after implantation, after about 10% of the period in which the active ingredient in the liquid formulation (e.g., bupivacaine and/or lidocaine formulation) is effective, after about 20% of the period in which the active ingredient in the liquid formulation is effective, after about 30% of the period in which the active ingredient in the liquid formulation is effective, after about 40% of the period in which the active ingredient in the liquid formulation is effective, after about 50% of the period in which the active ingredient in the liquid formulation is effective, after about 60% of the period in which the active ingredient in the liquid formulation is effective, after about 70% of the period in which the active ingredient in the liquid formulation is effective, after about 80% of the period in which the active ingredient in the liquid formulation is effective, after about 90% of the period in which the active ingredient in the liquid formulation is effective, after about 95% of the period in which the active ingredient in the liquid formulation is effective, or after about 99% of the period in which the active ingredient in the liquid formulation is effective.

Because the release of the active ingredient of the drug depot may be controlled through for example the inclusion of certain polymers that are known to facilitate extended release of active ingredients, in some embodiments, one could implant the drug depot prior to administering the liquid formulation while maintaining the ability to commence the release of the active ingredient in the drug depot to begin at a desired time, including after the injection of the liquid formulation.

Additionally, in some embodiments, the drug depot is introduced into the patient at least 10 seconds before or after the introduction of the liquid formulation (e.g., immediate release clonidine formulation), at least 1 minute before or after the introduction of the liquid formulation, at least 1 hour before or after the introduction of the liquid formulation, at least 2 hours before or after the introduction of the liquid formulation, at least 3 hours before or after the introduction of the liquid formulation, at least 4 hours before or after the introduction of the liquid formulation. In some embodiments the drug depot is introduced into the organism less than 10 seconds before or after the introduction of the liquid formulation, less than 20 seconds before or after the introduction of the liquid formulation, less than 1 minute before or after the introduction of the liquid formulation, less than 5 minutes before or after the introduction of the liquid formulation, less than 10 minutes before or after the introduction of the liquid formulation, less than 15 minutes before or after the introduction of the liquid formulation, less than 20 minutes before or after the introduction of the liquid formulation, less than 25 minutes before or after the introduction of the liquid formulation, less than 30 minutes before or after the introduction of the liquid formulation, less than 35 minutes before or after the introduction of the liquid formulation, less than 40 minutes before or after the introduction of the liquid formulation, less than 45 minutes before or after the introduction of the liquid formulation, less than 55 minutes before or after the introduction of the liquid formulation, less than 60 minutes before or after the introduction of the liquid formulation, less than 1 hour before or after the introduction of the liquid formulation, less than 2 hours before or after the introduction of the liquid formulation, less than 3 hours before or after the introduction of the liquid formulation, or less than 4 hours before or after the introduction of the liquid formulation.

Figure 2:
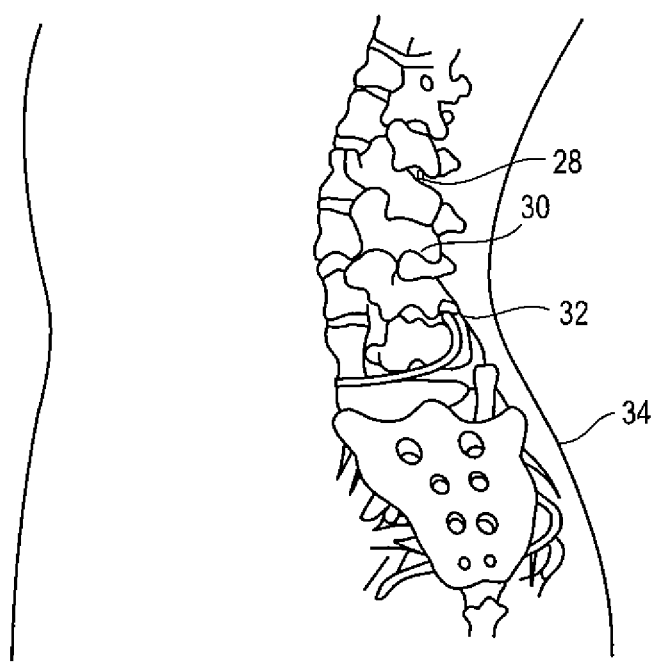
FIG. 2 illustrates a schematic dorsal view of the spine and sites where the injectable bupivacaine, and/or lidocaine formulation and the drug depot can locally be administered thereto.

One exemplary embodiment where the bupivacaine and/or lidocaine injection and drug depot are suitable for use in pain management (e.g., neuropathic pain management) and/or to treat conditions (e.g., sciatica) is illustrated in FIG. 2. Schematically shown in FIG. 2 is a dorsal view of the spine and sites where the bupivacaine and/or lidocaine injection and drug depot (containing the sustained release clonidine) may be inserted using a cannula or needle beneath the skin 34 to a spinal site 32 (e.g., spinal disc space, spinal canal, soft tissue surrounding the spine, nerve root, etc.) and one or more drug depots 28 and 32 are delivered to various sites along the spine. In this way, when the bupivacaine and/or lidocaine formulation and several drug depots are to be implanted, they are implanted in a manner that optimizes location, accurate spacing, and drug distribution. In some embodiments, the bupivacaine and/or lidocaine and the drug depots can be administered with one needle. In some embodiments, the bupivacaine and/or lidocaine is administered first and then the drug depot (containing sustained release clonidine) or they can be administered together or the drug depot first and then the bupivacaine and/or lidocaine injection. In some embodiments, the bupivacaine and/or lidocaine and/or depot can be administered using a subpedicular or retroneural technique.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal. Similarly, the clonidine can be administered at or near these locations. Further, in some embodiments, the clonidine is administered at a location closer to the target site than where the clonidine drug depot is placed.

By combining this depot with a one-time bupivacaine and/or lidocaine injection, a patient can obtain the acute benefits of a bupivacaine and/or lidocaine injection while receiving more sustained analgesia from the clonidine depot while avoiding the tissue-damaging effects of multiple bupivacaine and/or lidocaine injections.

In practice, the clonidine depot will be placed adjacent to the irritated nerve root or spinal nerve using a transforaminal approach with an 18 G spinal needle. At the same time the depots are delivered, a single bolus of bupivacaine and/or lidocaine will be delivered through the same needle.

Figure 3:
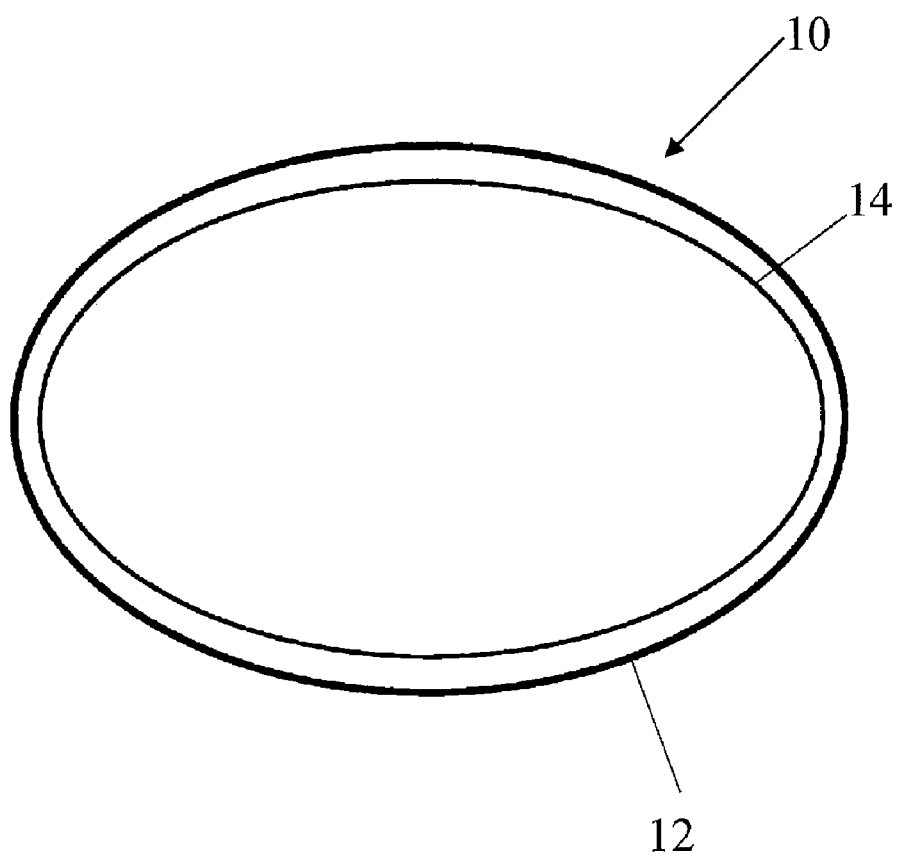
FIG. 3 is a schematic drawing illustrating an embodiment of one drug depot composition having a first region or layer capable of releasing a therapeutically effective bolus amount of bupivacaine, and/or lidocaine and a second region capable of releasing a therapeutically effective amount of the clonidine over a longer period of time.

FIG. 3 is a schematic drawing illustrating an embodiment of one drug depot 10 composition having a first region or layer 12 capable of releasing a therapeutically effective burst amount or bolus dose or pulse dose or immediate release of the bupivacaine and/or lidocaine as the depot comes in contact with the bodily fluid and the layer or region degrades and releases the clonidine. In this way, short-term relief of pain and/or inflammation can be provided to the patient. A second layer or region (shown as the core) of the depot shown as 14 is capable of releasing clonidine over a longer period of time (e.g, at least 3 days to 6 months) as this region or layer comes into contact with bodily fluid.

Although the initial burst region or layer is shown separately from the sustained release layer, it will be understood that the initial burst region or layer may be combined with the sustained release region or layer and thus when fluid contacts the depot each layer will release at different release rates. It will also be understood that, although the depot is shown with two layers or regions (12 and 14), the depot may comprise one or multiple layers or regions (e.g., two, three, four, five, six, seven, eight, nine ten, etc.). For example, a first immediate release layer or region may be disposed on a first sustained release layer and a second immediate release layer may be disposed on the first sustained release layer, and so on. It will also be understood that the depot may be formed from a mixture of a sustained release formulation with a burst release formulation that are combined together.

For example, the depot may be formed from separate different micelles (one or more bolus release micelle and one or more sustained release micelles) having different release profiles that are combined together. In various embodiments, the plurality of depots may comprise biodegradable therapeutic particles dispersed within a gel and as the gel degrades, the therapeutic particles are released.

Figure 4:
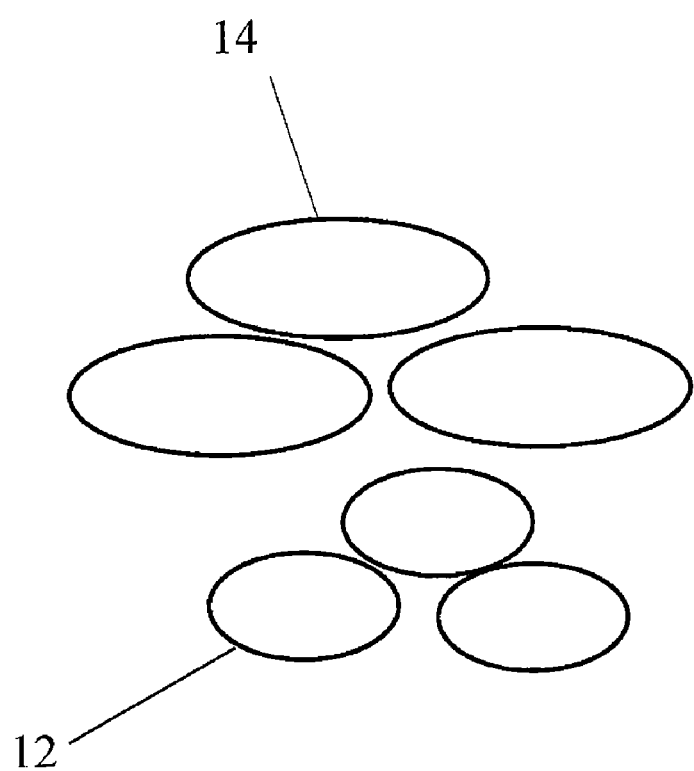
FIG. 4 is a schematic drawing illustrating an embodiment of a plurality of drug depots, a first set of drug depots capable of releasing a therapeutically effective bolus amount of bupivacaine, and/or lidocaine and a second set of drug depots capable of releasing a therapeutically effective amount of the clonidine over a longer period of time.

FIG. 4 is a schematic drawing illustrating an embodiment of a plurality of drug depots, a first set of drug depots 12 capable of releasing a therapeutically effective burst amount or bolus dose or pulse dose or immediate release of the bupivacaine and/or lidocaine and a plurality of depots 14 capable of releasing a therapeutically effective amount of the clonidine over a longer period of time (sustained release). Thus, in this embodiment, there is a set of drug depots. One set may comprising bupivacaine and/or lidocaine that has a burst release or bolus release or pulse release or immediate release and the other set containing the clonidine may be sustained release over a longer period of time. Thus, the first and second depot set have different release profiles. In this embodiment, a number of pellets for different diseases/conditions (e.g., sciatica, herniated disc pain etc.) with various drug release kinetics, some with fast release and other with slow release can be implanted together thus avoiding the need for one drug depot with complicated release kinetics.

In some embodiments, none of the depots (immediate and sustained release depots) contain a disintegrating agent. In some embodiments, only the sustained release depots contain a disintegrating agent.

In some embodiments, it is preferable to co-administer clonidine with an antagonist to counteract undesirable effects, for example the blood pressure decrease that can be caused by clonidine. Exemplary antagonists include but are not limited to phentolamine, yohimbine, tolazoline and piperoxane. Additionally, compounds such as 5-fluorodeoxyuridine (FUDR) and 3,4 dehydroprolene may also be included. These compounds may prevent or reduce glial and fibroblastic scar formation associated with some types of surgeries.

The clonidine, bupivacaine and/or lidocaine formulation of the present application may be used as medicaments in the form of pharmaceutical preparations. The preparations may be formed in an administration with a suitable pharmaceutical carrier that may be solid or liquid and organic or inorganic, and placed in the appropriate form for parenteral or other administration as desired. As persons of ordinary skill are aware, known carriers include but are not limited to water, saline solution, gelatin, lactose, starches, stearic acid, magnesium stearate, sicaryl alcohol, talc, vegetable oils, benzyl alcohols, gums, waxes, propylene glycol, polyalkylene glycols and other known carriers for medicaments.

Parenteral administration may additionally include, for example, an infusion pump that administers a pharmaceutical composition (e.g., analgesic and anti-inflammatory combination) through a catheter near the spine or one or more inflamed joints, an implantable mini-pump that can be inserted at or near the target site, an implantable controlled release device or sustained release delivery system that can release a certain amount of the bupivacaine and/or lidocaine per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas that provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, continually, at specific times, or at set intervals between deliveries.

Another embodiment is directed to a method for treating a mammal suffering from pain, said method comprising administering a therapeutically effective amount of bupivacaine and/or lidocaine at a target site beneath the skin. The bupivacaine and/or lidocaine (or pharmaceutically acceptable salt) may for example be administered locally to the target tissue site as a drug depot.

In some embodiments, the bupivacaine, lidocaine, and/or clonidine is encapsulated in a plurality of depots comprising microparticles, microspheres, microcapsules, and/or microfibers.

In some embodiments there is a method for making an implantable drug depot. The method may comprise combining a biocompatible polymer and a therapeutically effective amount of bupivacaine, lidocaine, and/or clonidine or a pharmaceutically acceptable salt thereof and forming the implantable drug depot from the combination.

In some embodiments, the clonidine is suitable for parenteral administration. The term "parenteral" as used herein refers to modes of administration that bypass the gastrointestinal tract, and include for example, intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof. In some embodiments, the injection is intrathecal, which refers to an injection into the spinal canal (intrathecal space surrounding the spinal cord). An injection may also be into a muscle or other tissue.

In various embodiments, the drug depot comprising the bupivacaine, lidocaine, and/or clonidine can be made by combining a biocompatible polymer and a therapeutically effective amount of bupivacaine, lidocaine, and/or clonidine or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: clonidine and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: clonidine, optional additional therapeutic agent(s), radiographic agent(s), and so forth. The resulting mixture is then shaped into an implantable drugdepot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, clonidine may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the clonidine containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of clonidine because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet) is cooled. Examples of cooling processes include air cooling and/or immersion in a cooling bath. In some embodiments, a water bath is used to cool the extruded depot. However, where a water-soluble therapeutic agent such as clonidine are used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape. In various embodiments, clonidine is used and mixed or sprayed with the PLGA or PEG550 polymer, and the resulting depot may be formed by extrusion and dried.

In various embodiments, there is a pharmaceutical formulation comprising: bupivacaine, lidocaine, and/or clonidine, wherein the bupivacaine, lidocaine, and/or clonidine comprises from about 0.1 wt. % to about 30 wt. % of the formulation, and at least one biodegradable polymer. In some embodiments, the bupivacaine, lidocaine, and/or clonidine comprises from about 3 wt. % to about 20 wt. %, about 3 wt. % to about 18 wt. %, about 5 wt. % to about 15 wt. % or about 7.5 wt. % to about 12.5 wt. % of the formulation. By way of example, when using a 5%-15% bupivacaine, lidocaine, and/or clonidine composition, the mole ratio of bupivacaine, lidocaine, and/or clonidine to polymer would be from approximately 16-53 when using an approximately 80 kDalton polymer that has a 267 grams/mole ratio. By way of another example, when using a 5%-15% bupivacaine, lidocaine, and/or clonidine base in the composition, the mole ratio of bupivacaine, lidocaine, and/or clonidine base to polymer would be from approximately 18-61 with a mole mass of 230 g/mol.

In some embodiments, the drug depot comprises at least one biodegradable material in a wt % of about 99.5%, 99%, 98%, 97%, 96%, 95%, 94%, 93%, 92%, 91%, 90%-89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot and the remainder is active and/or inactive pharmaceutical ingredients.

In some embodiments, the at least one biodegradable polymer comprises poly(lactic-co-glycolide) (PLGA) or poly(orthoester) (POE) or a combination thereof. The poly(lactic-co-glycolide) may comprise a mixture of polyglycolide (PGA) and polylactide and in some embodiments, in the mixture, there is more polylactide than polyglycolide. In various embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In some embodiments, the polymer in the depot comprises L-lactide-co-ϵ-caprolactone, or D,L-lactide-co-ϵ-caprolactone.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In various embodiments, the drug particle size (e.g., bupivacaine, lidocaine, and/or clonidine) is from about 5 to 30 micrometers, however, in various embodiments ranges from about 1 micron to 250 microns may be used. In some embodiments, the biodegradable polymer comprises at least 50 wt. %, at least 60 wt. %, at least 70 wt. %, at least 80 wt. % of the formulation, at least 85 wt. % of the formulation, at least 90 wt. % of the formulation, at least 95 wt. % of the formulation or at least 97 wt. % of the formulation. In some embodiments, the at least one biodegradable polymer and the clonidine are the only components of the pharmaceutical formulation.

In some embodiments, at least 75% of the particles have a size from about 10 micrometer to about 200 micrometers. In some embodiments, at least 85% of the particles have a size from about 10 micrometer to about 200 micrometers. In some embodiments, at least 95% of the particles have a size from about 10 micrometer to about 200 micrometers. In some embodiments, all of the particles have a size from about 10 micrometer to about 200 micrometers.

In some embodiments, at least 75% of the particles have a size from about 20 micrometer to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles have a size from about 20 micrometer to about 180 micrometers.

In some embodiments, at least 80% of the particles have a size from 5 microns to about 100 microns on a volume basis.

In some embodiments, there is a pharmaceutical formulation comprising: bupivacaine, lidocaine, and/or clonidine, wherein the bupivacaine, lidocaine, and/or clonidine is in the form of a hydrochloride salt, and comprises from about 0.1 wt. % to about 30 wt. % of the formulation, and at least one biodegradable polymer, wherein the at least one biodegradable polymer comprises poly(lactide-co-glycolide) (or poly (lactic-co-glycolic acid)) or poly(orthoester) or a combination thereof, and said at least one biodegradable polymer comprises at least 70 wt. % of said formulation.

In some embodiments, the drug depot comprises about 95 wt % poly(D,L-lactide) and 5 wt % clonidine HCl where the polymer has an ester end group and 70,000 daltons MW and an IV 0.45-0.55 dL/g and has a burst release of under 10% of the amount of drug in the depot within 24 hours (e.g., 5-10%) or 2-40 mcg in 24 hours. This formulation has 50% of total cumulative dose remaining for at least 60 days. About 80% of the particles in this depot including the clonidine are from about 5 to about 150 microns or 5-100 microns. The depot releases about 0.5 micrograms/day up to about 5 mcg/day of clonidine in 24 hours and then continues for 70 days.

In some embodiments, the drug depot comprises about 92 wt % poly(D,L-lactide) and 8 wt % clonidine HCl where the polymer has an ester end group and the polymer comprises 70,000 daltons MW and an IV of about 0.45-0.55 dL/g and has a burst release of under 10% of the amount of drug in the depot within 24 hours (e.g., 5-10%) or 5-6 mcg in 24 hours and then 1 to 20 mcg/day with a constant release for about 50 days, and then about 0.1 mcg to about 10 mcg/day for 70 days. This formulation has 50% of total cumulative dose remaining for at least 30-42 days and less than 80% cumulative drug release by 70 days. About 80% of the particles in this depot including the clonidine are from about 5 to about 150 microns or 5-100 microns.

In some embodiments, the drug depot comprises about 85 wt % poly(D,L-lactide) and 15 wt % clonidine HCl where the polymer has an ester end group and the polymer comprises 70,000 daltons MW and an IV of about 0.45-0.55 dL/g and has a burst release of under 10% of the amount of drug in the depot within 24 hours (e.g., 5-10%) or 20-150 mcg in 24 hours and then 5 to 80 mcg/day with a constant release for about 30 days, and then about 0.1 mcg to about 5 mcg/day for 70 days. This formulation has about 80% of total cumulative dose released within 35 days and 20% over several months. About 80% of the particles in this depot including the clonidine are from about 5 to about 150 microns or 5-100 microns.

In some embodiments, the drug depot comprises about a polymer having 60 mole % poly L-lactide and 40 mole % caprolactone, where the poly(L-lactide-co-caprolactone) has a MW of 30,000 to 35,000 daltons and an IV of about 0.5-0.6 dL/g and has a burst release of under 25% of the amount of drug in the depot within 24 hours (e.g., 5-15% within 4 hours). The drug depot comprises clonidine in an amount of 3-8 wt. %. The depot releases 400 mcg to about 1000 mcg for 7 days, which is about 40 mcg/day. This depot does not contain excipients. The clonidine has a particle size of 5 microns or less and 90% VD less than 20 microns. The degradation time in the body is not more than 3 months and the drug depot releases all of the clonidine within 2 weeks.

In some embodiments, the drug depot comprises about a polymer having 10 mole % poly D-L-lactide and 90 mole % caprolactone, where the poly(D,L-lactide-co-caprolactone) has a MW of 50,000 to 125,000 daltons and an IV of about 0.6 dL/g and has a burst release of under 25% of the amount of drug in the depot within 24 hours (e.g., 5-15% within 4 hours). The drug depot comprises clonidine in an amount of 3-10 wt. %. The depot releases 400 mcg to about 1000 mcg for 7 days, which is about 40 mcg/day. This depot contains from about 1% to about 5% by weight of mannitol or trehalose as a pore forming agent or plasticizer. The clonidine has a particle size of 5 microns or less and 90% VD less than 20 microns. The degradation time in the body is not more than 3 months and the drug depot releases all of the clonidine within 2 weeks. As you dropped the drug load the release was faster.

In some embodiments, the drug depot comprises clonidine and a GABA compound that is in the drug depot in an amount of from about 0.1% to about 75% by weight.

In some embodiments, when the drug depot comprises a GABA compound in the drug depot, the GABA compound is in the drug depot in an amount of from about 0.1% to about 75% by weight.

In some embodiments, the drug depot comprises both a GABA compound and clonidine in a single formulation. In some embodiments, the GABA compound can be in a separate depot from the clonidine.

In some embodiments, a GABA compound, a steroid, bupivacaine, lidocaine and/or clonidine can be administered in an immediate release or sustained release liquid by injection before, after, or during the administration of the clonidine depot.

In some embodiments, there is a pharmaceutical formulation comprising bupivacaine, lidocaine, and/or clonidine, wherein the bupivacaine, lidocaine, and/or clonidine is in a mixture of bupivacaine, lidocaine, and/or clonidine hydrochloride and bupivacaine, lidocaine, and/or clonidine base and the mixture comprises from about 0.1 wt. % to about 30 wt. % of the formulation and a polymer comprises at least 70% of the formulation. In some embodiments, the polymer in this formulation is polyorthoester.

In some embodiments, the formulation comprises a drug depot that comprises a biodegradable polyorthoester. The mechanism of the degradation process of the polyorthoester can be hydrolytical or enzymatical in nature, or both. In various embodiments, the degradation can occur either at the surface of the drug depot (heterogeneous or surface erosion) or uniformly throughout the drug delivery system depot (homogeneous or bulk erosion). Polyorthoester can be obtained from A.P. Pharma, Inc. (Redwood City, Calif.) or through the reaction of a bis(ketene acetal) such as 3,9-diethylidene-2,4,8,10-tetraoxospiro[5,5]undecane (DETOSU) with suitable combinations of diol(s) and/or polyol(s) such as 1,4-trans-cyclohexanedimethanol and 1,6-hexanediol or by any other chemical reaction that produces a polymer comprising orthoester moieties.

In some embodiments, the drug depot comprises 80% (w/w) ground PLGA50501A, 5% (w/w) spray dried clonidine HCl, 25% (w/w) bupivacaine or lidocaine base and 10% (w/w) mPEG (1:5 ratio). In some embodiments, the drug depot comprises 80% (w/w) ground PLGA50501A, 2% (w/w) spray dried clonidine HCl, 25% (w/w) bupivacaine base or lidocaine base and 10% (w/w) mPEG (1:12.5 ratio). In a third embodiment, the drug depot comprises 80% (w/w) ground PLGA50501A, 1% (w/w) spray dried clonidine HCl, 25% (w/w) bupivacaine base or lidocaine base, and 10% (w/w) mPEG (1:25 ratio).

In some embodiments, there are methods for treating acute pain. These methods comprise: administering a pharmaceutical composition to an organism, wherein said pharmaceutical composition (e.g., bupivacaine, lidocaine, and/or clonidine) comprises from about 0.1 wt. % to about 30 wt. % of the formulation, and at least one biodegradable polymer. In some embodiments, the loading is from about 1 wt % to about 25 wt %, or about 5 wt. % to about 10 wt. %. In some embodiments, the loading is from about 10 wt. % to about 20 wt. %.

In some embodiment there is a higher loading of bupivacaine, lidocaine, and/or clonidine, e.g., at least 20 wt. %, at least 30 wt. %, at least 40 wt. %, at least 50 wt. %, at least 60 wt. %, at least 70 wt. %, at least 80 wt. %, or at least 90 wt. %.

A strategy of triangulation may be effective when administering these pharmaceutical formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In some embodiments, the formulations are slightly rigid with varying length, widths, diameters, etc. For example, certain formulations may have a diameter of 0.50 mm and a length of 4 mm. It should be noted that particle size may be altered by techniques such as mort and pestle, jet-drying or jet milling.

In some embodiments, clonidine is released at a rate of 2-3 μg per day for a period of at least three days. In some embodiments, this release rate continues for, at least ten days, at least fifteen days, at least twenty-five days, at least fifty days, at least ninety days, at least one hundred days, at least one-hundred and thirty-five days, at least one-hundred and fifty days, or at least one hundred and eighty days. For some embodiments, 300-425 micrograms of clonidine as formulated with a biopolymer are implanted into a person at or near a target tissue site. If clonidine is implanted at multiple sites that triangulate the target site then in some embodiments, the total amount of clonidine at each site is a fraction of the total 300-425 micrograms. For example, one may implant a single dose of 324 micrograms at one site, or two separate doses of 162 micrograms at two sites, or three separate dose of 108 micrograms at three sites that triangulate the tissue site. It is important to limit the total dosage to an amount less than that which would be harmful to the organism. However, in some embodiments, although when there are a plurality of sites each site may contain less than the total dose that might have been administered in a single application, it is important to remember that each site will independent have a release profile, and the biopolymers' concentration and substance should be adjusted accordingly to ensure that the sustain release occurs over sufficient time.

The dosage of clonidine may be from approximately 0.0005 to approximately 960 μg/day. Additional dosages of clonidine include from approximately 0.0005 to approximately 900 μg/day; approximately 0.0005 to approximately 500 μg/day; approximately 0.0005 to approximately 250 μg/day; approximately 0.0005 to approximately 100 μg/day; approximately 0.0005 to approximately 75 μg/day; approximately 0.001 to approximately 70 μg/day; approximately 0.001 to approximately 65 μg/day; approximately 0.001 to approximately 60 μg/day; approximately 0.001 to approximately 55 μg/day; approximately 0.001 to approximately 50 μg/day; approximately 0.001 to approximately 45 μg/day; approximately 0.001 to approximately 40 μg/day; approximately 0.001 to approximately 35 μg/day; approximately 0.0025 to approximately 30 μg/day; approximately 0.0025 to approximately 25 μg/day; approximately 0.0025 to approximately 20 μg/day; approximately 0.0025 to approximately 15 μg/day; approximately 0.0025 to approximately 10 μg/day; approximately 0.0025 to approximately 5 μg/day; and approximately 0.0025 to approximately 2.5 μg/day. In another embodiment, the dosage of clonidine is from approximately 0.005 to approximately 15 μg/day. In another embodiment, the dosage of clonidine is from approximately 0.005 to approximately 10 μg/day. In another embodiment, the dosage of clonidine is from approximately 0.005 to approximately 5 μg/day. In another embodiment, the dosage of clonidine is from approximately 0.005 to 2.5 μg/day. In some embodiments, the amount of clonidine is between 40 and 600 μg/day. In some embodiments, the amount of clonidine for the bolus dose is between 200 and 400 μg/day.

In some embodiments, the therapeutically effective dosage amount (e.g., bupivacaine, lidocaine, and/or clonidine dose) and the release rate profile are sufficient to reduce inflammation and/or pain for a period of at least one day, for example, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, 14-140 days, 3 days to 135 days, 3 days to 180 days, or 3 days to 6 months or 1 year or longer.

In some embodiments the bupivacaine and/or lidocaine in the depot is designed for a bolus dose or burst dose within 1, 2, or 3 days after implantation to provide an immediate release of the bupivacaine and/or lidocaine for treatment of pain and/or inflammation.

In some embodiments, the bupivacaine, lidocaine and/or clonidine depot is administered parenterally, e.g., by injection. In some embodiments, the injection is intrathecal, which refers to an injection into the spinal canal (intrathecal space surrounding the spinal cord). An injection may also be into a muscle or other tissue. In other embodiments, the bupivacaine, lidocaine and/or clonidine depot is administered by placement into an open patient cavity during surgery.

In some embodiments, the drug depot (i) comprises one or more immediate release layer(s) that is capable of releasing about 5% to about 20% of the bupivacaine, and/or lidocaine relative to a total amount of the bupivacaine, and/or lidocaine loaded in the drug depot over a first period of up to 48 hours and (ii) one or more sustain release layer(s) that is capable of releasing about 21% to about 99% of the clonidine or pharmaceutically acceptable salt thereof relative to a total amount of the clonidine or pharmaceutically acceptable salt thereof loaded in the drug depot over a subsequent period of up to 3 days to 90 days, 150 days, 180 days, or 6 months to 1 year.

In some embodiments, there is a drug depot comprising bupivacaine, lidocaine or clonidine and a polymer, wherein the polymer is one more of various embodiments, the drug depot comprises poly(lactide-co-glycolide) (PLGA), polylactide (PLA), polyglycolide (PGA), D-lactide, D,L-lactide, L-lactide, D,L-lactide-co-$\epsilon$-caprolactone, D,L-lactide-co-glycolide-co-$\epsilon$-caprolactone or a combination thereof.

In one exemplary dosing regimen, a rat may be provided with sufficient clonidine in a biodegradable polymer to provide sustain release of 0.240 µg/day for 135 days. The total amount of clonidine that is administered over this time period would be approximately 32.4 µg. In another exemplary dosing regimen, a human is provided with sufficient clonidine in a biodegradable polymer to provide sustain release of 2.4 µg/day for 135 days. The total amount of clonidine that is administered over this time period would be approximately 324 µg. In another exemplary dosing regimen, a human is provided with sufficient clonidine in a biodegradable polymer to provide sustain release of 0.5 µg/day to about 5 µg/day in 24 hours, continuing for 70 days. When using a plurality of pellets, the pellet number is based on the amount of drug loading into a pellet of appropriate size (i.e., 0.5 mm diameter×4 mm length) and how much drug is needed (e.g., approximately 325 µg clonidine (3 pellets)). In some embodiments, 3 to 6 pellets are used. In some embodiments there is a polymer that releases a bolus amount of compound over the first few (~5) days before it settles down and releases 2.5 mg/day for 135 days. An exemplary formulation is 5% wt. clonidine, 100 DL 5E (Lakeshore Biomaterials, Birmingham, Ala.).

In some embodiments, the polymer depots of present invention enable one to provide efficacy of the active ingredient that is equivalent to subcutaneous injections that deliver more than 2.5 times as much drug.

Having now generally described the invention, the same may be more readily understood through the following reference to the following examples, which are provided by way of illustration and are not intended to limit the present invention unless specified.

EXAMPLES

The drug depot containing clonidine, bupivacaine and/or lidocaine depot can be given with bolus doses of bupivacaine, lidocaine and/or steroids as discussed in the International Spine Intervention Society (ISIS) guidelines listed below.

Agents for Injection:

Water soluble, non-ionic radiographic contrast medium suitable for intravascular and intrathecal use (e.g. Omnipaque or Isovue M-200)

Preservative free local anesthetics, in volumes of 3.0 ml to 5.0 ml, such as lidocaine 1%-2%, or bupivacaine 0.125%-0.50%

A depot corticosteroid preparation, such as:

Betamethasone (Celestone® Soluspan) 6-18 mg

Triamcinolone 20-80 mg

Dexamethasone

Techniques:

Subpedicular

Retroneural

Advantages of Subpedicular Technique

Relies less on judgment to establish that the needle has reached the target point. The target point is an osseous landmark that can be identified manually by resistance to the passage of the needle, and visually by recognizing the back of the vertebral body on lateral fluoroscopic views. It is also the technique that has been used in all the observational and controlled studies Disadvantages of Subpedicular Technique:

The perceived disadvantage is the remote risk of intra-arterial injection. Heeding a report that complications might be caused if particulate steroids were injected into the radicular artery, operators elected to avoid the floor of the intervertebral foramen where the radicular artery is presumed most often to lie Advantages of Retroneural Technique:

It avoids anterior radicular arteries.

Disadvantage of Retroneural Technique:

It requires judgment to achieve correct placement of the needle and not puncture the target nerve or dural sheath.

Technically, there is no evidence that this approach is effective as the subpedicular approach Injection:

Once the target point has been correctly reached, a test dose of contrast medium should be injected (0.2-0.5 ml), sufficient to determine that the contrast medium has not been injected intrathecally or intravascularly.

If the contrast medium reveals that a radicular artery or the thecal sac has been injected, the procedure should be terminated, and resumed on another occasion to allow the puncture to heal. If the contrast medium reveals intravenous injection, the needle should be readjusted slightly, and the injection of a test-dose of contrast medium should be repeated.

If and once the injection of a test dose of contrast medium indicates that the injection of contrast medium is not intrathecal or intravascular, a further injection of contrast medium should be performed. Prior to injection, the volume on the syringe containing the contrast medium should be noted. Optimally, the contrast medium should fill the "safe triangle" and spread medially, following the course of the nerve root sleeve. Some may spread peripherally following the ventral ramus, but most of it should spread centrally.

If too much of the contrast medium spreads peripherally, the injection should be terminated, and the needle should be readjusted to a slightly more medial position. If the needle is readjusted, a test-dose of contrast medium should be repeated in order to check for intravascular or intrathecal placement, before proceeding with the definitive injection of contrast medium.

Once the target nerve is considered to have been adequately "covered" by contrast medium, and the injection has been terminated, the remaining volume of contrast medium in the syringe is read, and the total volume of contrast medium injected is calculated. This volume will constitute the prescribed volume of therapeutic agent to be injected in the next step.

The syringe containing the contrast medium is replaced with one containing the therapeutic agent or agents. If a mixture of local anesthetic and corticosteroid preparation is used, the prescribed volume of the mixture can be injected. If local anesthetic and corticosteroids are to be injected separately, the local anesthetic is injected first, to a volume not exceeding half the prescribed volume. The corticosteroid preparation is injected next, up to a volume equal to the prescribed volume. Once injected, the needle or needles are withdrawn and the procedure has been completed.

Performance Parameters

The procedure should normally be completed with only one skin puncture, but a maximum of two. The needle should not need to be redirected more than eight times, unless unusual anatomy confounds the procedures, or if venous injection is encountered.

The target point should be identified within less than 30 seconds of radiation exposure time. No more than 30 seconds of additional radiation exposure time should be required to perform a transforaminal epidural injection at a single level. In the presence of unusual anatomy, or in the event of venous injection, up to 45 seconds of radiation exposure time may be required to complete the procedure.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable drug depot useful for reducing or treating pain in a patient in need of such treatment, the implantable drug depot comprising about 0.1 wt % to about 30 wt % of clonidine, about 15 wt % to about 60 wt % of bupivacaine or about 0.1 wt % to about 30 wt % of lidocaine and a biodegradable polymer, the depot being implantable at a site beneath the skin to reduce or treat pain, wherein the drug depot comprises (i) at least one region capable of releasing a therapeutically effective bolus dose of the bupivacaine or lidocaine at a site beneath the skin, the at least one region including about 1 to about 5 wt % of at least one of mannitol or trehalose; and (ii) at least one sustained release region capable of releasing a therapeutically effective amount of the clonidine over a period of at least three days, wherein the bupivacaine or lidocaine is not released in a sustained dose and the clonidine is not released in a bolus dose.

2. An implantable drug depot according to claim 1, wherein (i) the bolus dose of bupivacaine or lidocaine is released within 30 minutes to 24 hours and the sustained release region releases the clonidine over a period of 3 days to 6 months or wherein the bolus dose of bupivacaine or lidocaine is released within 30 minutes to 14 days and the sustained release region releases the clonidine over a period of 3 days to 6 months.

3. An implantable drug depot according to claim 1, wherein the biodegradable polymer comprises at least 85 wt. % of the drug depot.

4. An implantable drug depot according to claim 1, wherein (i) the biodegradable polymer comprises polylactide or (ii) the biodegradable polymer comprises one or more of poly (lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L lactide-co-glycolide-co-ε-caprolactone or a combination thereof.

5. An implantable drug depot according to claim 3, wherein the biodegradable polymer comprises poly(lactic-co-glycolide) and said poly(lactic-co-glycolide) comprises a mixture of polyglycolide and polylactide.

6. An implantable drug depot according to claim 5, wherein the biodegradable polymer comprises more polylactide than polyglycolide and the clonidine is an insoluble salt of clonidine comprising a fatty acid salt.

7. An implantable drug depot according to claim 1, wherein the pain is at least one of radicular pain, pain from disc herniation or pain from sciatica.

8. A kit comprising a plurality of implantable drug depots useful for reducing or treating pain in a patient in need of such treatment, the kit comprising (i) a first set of the plurality of drug depots comprising a biodegradable polymer capable of releasing a therapeutically effective bolus dose of bupivacaine or lidocaine at a site beneath the skin and about 1 to about 5 wt % of at least one of mannitol or trehalose; and (ii) a second set of the plurality of drug depots comprising a second biodegradable polymer capable of providing sustained release of a therapeutically effective amount of the clonidine over a period of at least three days, wherein the bupivacaine or lidocaine is not released in a sustained dose and the clonidine is not released in a bolus dose.

9. A kit according to claim 8, wherein the bolus dose of bupivacaine or lidocaine is released within one to 24 hours and the clonidine is sustained released over a period of 3 days to 6 months.

10. A kit according to claim 8, wherein the biodegradable polymer comprises more polylactide than polyglycolide and the clonidine is an insoluble salt of clonidine comprising a fatty acid salt.

11. A kit according to claim 8, wherein the clonidine is in the form of clonidine hydrochloride or a mixture of clonidine base and a hydrochloride salt and the bupivacaine or lidocaine is in the form of a base or a salt.

12. A kit according to claim 8, wherein the biodegradable polymer comprises one or more of poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolideco-ε-caprolactone or a combination thereof.

13. A method for treating a mammal suffering from pain, the method comprising administering a therapeutically effective amount of an injectable bupivacaine or lidocaine and an implantable device comprising clonidine in an amount from about 0.1 wt. % to about 30 wt. % of the implantable device, and at least one biodegradable polymer, wherein the implantable device is capable of releasing clonidine over a period of at least three days and the implantable device includes about 1 to about 5 wt % of at least one of mannitol or trehalose, wherein the bupivacaine or lidocaine is not released in a sustained dose and the clonidine is not released in a bolus dose.

14. A method according to claim 13, wherein the injectable bupivacaine or lidocaine is administered before the implantable device and with a steroid.

15. A method according to claim 13, wherein the injectable bupivacaine or lidocaine is administered with or after the implantable device and with a steroid.

16. A method according to claim 13, wherein the injectable bupivacaine or lidocaine is an immediate release liquid.

17. A method according to claim 13, wherein biodegradable polymer comprises one or more of poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolideco-ε-caprolactone or a combination thereof.

18. A method according to claim 13, wherein the clonidine is in the form of clonidine hydrochloride or a mixture of clonidine base and a hydrochloride salt or the clonidine is an insoluble salt of clonidine comprising a fatty acid salt.

19. A method according to claim 13, wherein the bolus dose of bupivacaine is between about 50 mg to 500 mg or lidocaine is between about 10 mg to 100 mg.

20. An implantable drug depot according to claim 1, wherein the clonidine is a lipid soluble salt of clonidine.

* * * * *